US 7,994,187 B2

(12) United States Patent
Kesteleyn et al.

(10) Patent No.: US 7,994,187 B2
(45) Date of Patent: Aug. 9, 2011

(54) HIV INHIBITING 3,4-DIHYDRO-IMIDAZO[4,5-B]PYRIDIN-5-ONES

(75) Inventors: Bart Rudolf Romanie Kesteleyn, Berlare (BE); Wim Bert Griet Schepens, Wetteren (BE)

(73) Assignee: Tibotec Pharmaceuticals Ltd. (IE)

( * ) Notice: Subject to any disclaimer, the term of this patent is extended or adjusted under 35 U.S.C. 154(b) by 485 days.

(21) Appl. No.: 12/295,816

(22) PCT Filed: Apr. 3, 2007

(86) PCT No.: PCT/EP2007/053207
§ 371 (c)(1),
(2), (4) Date: Oct. 2, 2008

(87) PCT Pub. No.: WO2007/113290
PCT Pub. Date: Oct. 11, 2007

(65) Prior Publication Data
US 2009/0170855 A1    Jul. 2, 2009

(30) Foreign Application Priority Data

Apr. 3, 2006  (EP) .................... 06112173

(51) Int. Cl.
*A61K 31/4745*  (2006.01)
*C07D 471/14*  (2006.01)

(52) U.S. Cl. .......... 514/287; 546/64; 544/247; 544/233; 544/115; 514/248; 514/257

(58) Field of Classification Search ................. 514/287, 514/248, 257; 546/64; 544/247, 233, 115
See application file for complete search history.

(56) References Cited

U.S. PATENT DOCUMENTS 7,884,221 B2    2/2011  Kawachi

FOREIGN PATENT DOCUMENTS

| EP | 0 499 299 B1 | 8/1992 |
| EP | 0 721 331 B1 | 7/1996 |
| WO | WO 94/05263 A1 | 3/1994 |
| WO | WO 97/44014 A1 | 11/1997 |
| WO | WO 98/42318 A1 | 10/1998 |
| WO | WO 2004/046163 A1 | 6/2004 |
| WO | WO 2005/110411 A2 | 11/2005 |
| WO | WO 2005/111034 A1 | 11/2005 |
| WO | WO 2005/111035 A1 | 11/2005 |
| WO | WO 2005/111044 A1 | 11/2005 |
| WO | WO 2005/111047 A1 | 11/2005 |

OTHER PUBLICATIONS

International Search Report dated Jul. 6, 2007 for related International Application No. PCT/EP2007/053207.

*Primary Examiner* — Charanjit S Aulakh

(57) ABSTRACT

HIV inhibitory compounds of formula:

(I)

salts, hydrates, solvates, N-oxides, or stereoisomers thereof, wherein

A forms pyridine, pyrimidine, pyrazine, pyridazine, triazine, imidazole, pyrazole, triazole, tetrazole, oxazole, isoxazole, oxadiazole, thiazole, isothiazole, and thiadiazole;

$R^1$ is halo, cyano, nitro, $C_{1-6}$alkyl, polyhalo$C_{1-6}$alkyl, —$C_{1-6}$alkyl-$OR^4$, —C(=O)—$R^5$, —C(=O)—$OR^4$, —C(=O)—$NR^6R^7$, —$OR^4$, —O—C(=O)—$C_{1-6}$alkyl, —O—$C_{1-6}$alkyl-$OR^4$, —O—$C_{1-6}$alkyl-$NR^6R^7$, —O—$C_{1-6}$alkyl-O—C(=O)—$C_{1-6}$alkyl, —O—$C_{1-6}$alkyl-C(=O)—$OR^4$, —O—$C_{1-6}$alkyl-C(=O)—$NR^6R^7$, —$NR^6R^7$, —$NR^8$—C(=O)—$R^5$, —$NR^8$—C(=O)—$OR^4$, —$NR^8$—C(=O)—$NR^6R^7$, —$NR^8$—C(=O)—$C_{1-6}$alkyl-C(=O)—$OR^4$, —$NR^8$—$C_{1-6}$alkyl-$OR^4$, —$NR^8$—$C_{1-6}$alkyl-$NR^6R^7$, —$NR^8$—$C_{1-6}$alkyl-imidazolyl, —$NR^8$—$SO_2R^9$, —N=CH—$NR^6R^7$, —NH—C(=NH)—$NH_2$, —$SO_2NR^6R^7$, and —O—$PO(OR^8)_2$;

D forms pyridine, pyrimidine, pyrazine, pyridazine, pyrrole, imidazole, pyrazole, furane, oxazole, isoxazole, thiophene, thiazole, and isothiazole;

$R^2$ is $C_{1-6}$alkyl, polyhalo$C_{1-6}$alkyl, halo, cyano, —$COOR^4$, —$OR^4$, and —$NR^6R^7$;

$R^3$ is phenyl, pyridyl, pyrimidinyl, imidazopyridyl, pyrazolopyridyl, triazolopyridyl, quinoline, imidazopyrimidinyl, pyrazolopyrimidinyl, triazolopyrimidinyl, pyridopyrimidinyl; which may optionally be substituted;

m is 0, 1, 2 or 3; n is 0, 1, 2 or 3;

pharmaceutical compositions containing these compounds, methods for preparing these compounds and compositions.

11 Claims, No Drawings

HIV INHIBITING 3,4-DIHYDRO-IMIDAZO[4,5-B]PYRIDIN-5-ONES

CROSS REFERENCE TO RELATED APPLICATIONS

This application is a national stage application of Patent Application No. PCT/EP2007/053207, filed Apr. 3, 2007, which application claims priority from EPO Patent Application No. 06112173.7, filed Apr. 3, 2006, both of which are hereby incorporated by reference in their entirety.

This invention is directed to 3,4-dihydro-imidazo[4,5-b]pyridin-5-one derivatives, their use as anti-infective agents, and to pharmaceutical compositions containing these compounds.

The human immunodeficiency virus (HIV) is the aetiological agent of the acquired immunodeficiency syndrome (AIDS). Two distinct types of HIV have been identified, i.e. HIV-1 and HIV-3 and hereinafter, the term HIV is used to generically denote both these types. AIDS patients are currently treated with a variety of agents such as HIV reverse transcriptase inhibitors (RTIs), HIV protease inhibitors (PIs) and entry inhibitors. Several classes of RTIs are known, in particular the nucleoside reverse transcriptase inhibitors (NRTIs) such as zidovudine, didanosine, zalcibatine, stavudine, abacavir and lamivudine, the non-nucleoside reverse transcriptase inhibitors (NNRTIs) such as nevirapine, delavirdine and efavirenz, and the nucleotide reverse transcriptase inhibitors (NtRTIs) such as tenofovir.

Anti-HIV therapy is currently based on the administration of drug combinations comprising two or more agents of the above classes of drugs. Despite the fact that these antiretrovirals have been applied successfully, they have a common limitation in that the targeted enzymes in HIV are able to mutate in such a way that any of the known drugs become less effective, or even ineffective against these mutant HIV viruses. The HIV virus creates an ever-increasing resistance against any available drugs and the emergence of this resistance is a major cause of therapy failure. Moreover, it has been shown that resistant virus is carried over to newly infected individuals, resulting in severely limited therapy options for these drug-naive patients.

All RTIs give rise to the emergence of resistance and especially the currently used NNRTIs are sensitive to this phenomenon due to mutations at amino acids that surround the NNRTI-binding site. Hence there is a need for new types of HIV inhibitors that target HIV reverse transcriptase, which are able to delay the emergence of resistance and are effective against a broad spectrum of mutants of HIV.

WO-04/046163, WO-05/111034, WO-05/111035, WO-05/111047 and WO-05/111044 describe tricyclic 5-substituted 1-phenyl-1,5-dihydro-pyrido[3,2-b]indol-2-ones and various analogs thereof. Combinations of the compounds of WO-04/046163 with certain HIV inhibitors have been described in WO-05/110411.

The present invention provides a new series of compounds that are structurally different from the compounds of the prior art, and show activity not only against wild type HIV virus but also against a variety of mutant HIV viruses, including mutant HIV viruses showing resistance against currently available reverse transcriptase inhibitors.

Thus in one aspect, the present invention concerns 3,4-dihydro-imidazo[4,5-b]pyridin-5-one containing compounds of formula (I):

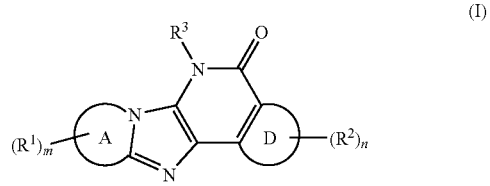

the stereoisomeric forms or stereoisomeric mixtures thereof, the pharmaceutically acceptable salts thereof, the pharmaceutically acceptable hydrates or solvates thereof, the N-oxides thereof, wherein A forms, together with the nitrogen and carbon atoms of the ring system to which it is attached, an aromatic heterocycle selected from pyridine, pyrimidine, pyrazine, pyridazine, triazine, imidazole, pyrazole, triazole, tetrazole, oxazole, isoxazole, oxadiazole, thiazole, isothiazole, and thiadiazole;

each $R^1$ is, independently, a radical selected from halo, cyano, nitro, $C_{1-6}$alkyl, polyhalo$C_{1-6}$alkyl, —$C_{1-6}$alkyl-$OR^4$, —C(=O)—$R^5$, —C(=O)—$OR^4$, —C(=O)—$NR^6R^7$, —$OR^4$, —O—C(=O)—$C_{1-6}$alkyl, —O—$C_{1-6}$alkyl-$OR^4$, —O—$C_{1-6}$alkyl-$NR^6R^7$, —O—$C_{1-6}$alkyl-O—C(=O)—$C_{1-6}$alkyl, —O—$C_{1-6}$alkyl-C(=O)—$OR^4$, —O—$C_{1-6}$alkyl-C(=O)—$NR^6R^7$, —$NR^6R^7$, —$NR^8$—C(=O)—$R^5$, —$NR^8$—C(=O)—$OR^4$, —$NR^8$—C(=O)—$NR^6R^7$, —$NR^8$—C(=O)—$C_{1-6}$alkyl-C(=O)—$OR^4$, —$NR^8$—$C_{1-6}$alkyl-$OR^4$, —$NR^8$—$C_{1-6}$alkyl-$NR^6R^7$, —$NR^8$—$C_{1-6}$alkyl-imidazolyl, —$NR^8$—$SO_2R^9$, —N=CH—$NR^6R^7$, —NH—C(=NH)—$NH_2$; —$SR^8$, —$SO_2NR^6R^7$, and —O—PO($OR^8$)$_2$;

D forms, together with the two carbon atoms of the ring system to which it is attached, an aromatic ring selected from phenyl, pyridine, pyrimidine, pyrazine, pyridazine, pyrrole, imidazole, pyrazole, furane, oxazole, isoxazole, thiophene, thiazole, and isothiazole;

each $R^2$ is, independently, a radical selected from $C_{1-6}$alkyl, polyhalo$C_{1-6}$alkyl, halo, cyano, —$COOR^4$, —$OR^4$, and —$NR^6R^7$;

$R^3$ is phenyl, pyridyl, pyrimidinyl, imidazopyridyl, pyrazolopyridyl, triazolopyridyl, quinoline, imidazopyrimidinyl, pyrazolopyrimidinyl, triazolopyrimidinyl, pyridopyrimidinyl; wherein said phenyl, pyridyl, or pyrimidinyl, may optionally be substituted with 1, 2, or 3 substituents selected from $C_{1-6}$alkyl; $C_{2-6}$alkenyl; $C_{2-6}$alkynyl; polyhalo$C_{1-6}$alkyl; $C_{1-6}$alkyl substituted with one or two cyano or hydroxy; halo; cyano; nitro; —C(=O)—$R^5$; —C(=O)—$OR^4$; —C(=O)—$NR^6R^7$; —$OR^4$; —$NR^6R^7$; and wherein said imidazopyridyl, pyrazolopyridyl, triazolopyridyl, quinoline, imidazopyrimidinyl, pyrazolopyrimidinyl, triazolopyrimidinyl, pyridopyrimidinyl, may optionally be substituted with 1 or 2 substituents selected from $C_{1-6}$alkyl, halo, amino, and —$OR^4$;

m represents 0, 1, 2 or 3;
n represents 0, 1, 2 or 3;
each $R^4$ is hydrogen, $C_{1-6}$alkyl or aryl$C_{1-6}$alkyl;
each $R^5$ is hydrogen, $C_{1-6}$alkyl or polyhalo$C_{1-6}$alkyl;
each $R^6$ is hydrogen or $C_{1-6}$alkyl;
each $R^7$ is hydrogen, $C_{1-6}$alkyl optionally substituted with hydroxy, aryl, mono- or di$C_{1-6}$alkylamino, morpholinyl, thiomorpholinyl, piperidinyl, piperazinyl, 4-$C_{1-6}$alkyl-piperazinyl, 4-$C_{1-6}$alkylcarbonyl-piperazinyl or with pyrrolidinyl; or $R^6$ and $R^7$ taken together with the nitrogen on which they are substituted form pyrrolidinyl, hydroxypyrrolidinyl, piperidinyl, morpholinyl, thiomorpholinyl, piperazinyl, 4-$C_{1-6}$alkyl-piperazinyl, 4-$C_{1-6}$alkylcarbonyl-piperazinyl;

each $R^8$ is hydrogen or $C_{1-6}$alkyl;

each $R^9$ is $C_{1-6}$alkyl;

each aryl is phenyl optionally substituted with 1, 2, or 3 substituents independently selected from $C_{1-6}$alkyl, halo, and hydroxy.

The term "$C_{1-4}$alkyl" as a group or part of a group defines straight and branched chained saturated hydrocarbon radicals having from 1 to 4 carbon atoms, such as, for example, methyl, ethyl, 1-propyl, 2-propyl, 1-butyl, 2-methyl-propyl and the like. The term "$C_{1-6}$alkyl" as a group or part of a group defines straight and branched chained saturated hydrocarbon radicals having from 1 to 6 carbon atoms such as, for example, the groups defined for $C_{1-4}$alkyl and 1-pentyl, 2-pentyl, 1-hexyl, 2-hexyl, 3-hexyl, 2-methylbutyl, 3-methylpentyl and the like. Of interest amongst $C_{1-6}$alkyl are the $C_{1-4}$alkyl radicals.

The radicals $C_{1-4}$alkyl and $C_{1-6}$alkyl may have two bonds such as, for example, in the radicals —O—$C_{1-6}$alkyl-$OR^4$, —O—$C_{1-6}$alkyl-$NR^6R^7$—$NR^8$—$C_{1-6}$alkyl-$OR^4$, —$NR^8$—$C_{1-6}$alkyl-$NR^6R^7$. Such bivalent $C_{1-4}$alkyl or $C_{1-6}$alkyl refers to bivalent radicals which otherwise can also be referred to as $C_{1-4}$alkanediyl or $C_{1-6}$alkanediyl. The term bivalent $C_{1-6}$alkyl or $C_{1-6}$alkanediyl defines straight or branched chain saturated bivalent hydrocarbon radicals having from 1 to 6 carbon atoms such as methylene, 1,2-ethanediyl or 1,2-ethylene, 1,3-propanediyl or 1,3-propylene, 1,2-propanediyl or 1,2-propylene, 1,4-butanediyl or 1,4-butylene, 1,3-butanediyl or 1,3-butylene, 1,2-butanediyl or 1,2-butylene, 1,5-pentanediyl or 1,5-pentylene, 1,6-hexanediyl or 1,6-hexylene, etc., also including the alkylidene radicals such as ethylidene, propylidene and the like. The term bivalent $C_{1-4}$alkyl or $C_{1-4}$alkanediyl defines the analogous straight or branched chain saturated bivalent hydrocarbon radicals having from 1 to 4 carbon atoms. Where the bivalent $C_{1-4}$alkyl or $C_{1-6}$alkyl is linked to two heteroatoms such as in —O—$C_{1-6}$alkyl-$OR^4$, —O—$C_{1-6}$alkyl-$NR^6R^7$, —$NR^8$—$C_{1-6}$alkyl-$OR^4$, —$NR^8$—$C_{1-6}$alkyl-$NR^6R^7$, the heteroatoms preferably are not bonded on the same carbon atom unless $R^4$, $R^6$, $R^7$ and $R^8$ are other than hydrogen. Of particular interest are bivalent $C_{2-4}$alkyl or bivalent $C_{2-6}$alkyl radicals.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Preferred are $C_{2-6}$alkenyls having one double bond. Of interest amongst $C_{2-6}$alkenyl radicals are the $C_{2-4}$alkyl radicals. The term "$C_{3-6}$alkenyl" is as $C_{2-6}$alkenyl but is limited to unsaturated hydrocarbon radicals having from 3 to 6 carbon atoms. In the instances where a $C_{3-6}$alkenyl is linked to a heteroatom, the carbon atom linked to the heteroatom by preference is saturated.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-methyl-2-propynyl, 2-pentynyl, 3-pentynyl, 2-hexynyl, 3-hexynyl, 4-hexynyl, 2-methyl-2-butynyl, 2-methyl-2-pentynyl and the like. Preferred are $C_{2-6}$alkynyls having one triple bond. Of interest amongst $C_{2-6}$alkynyl radicals are the $C_{2-4}$alkyl radicals. The term "$C_{3-6}$alkynyl" is as $C_{2-6}$alkynyl but is limited to unsaturated hydrocarbon radicals having from 3 to 6 carbon atoms. In the instances where a $C_{3-6}$alkynyl is linked to a heteroatom, the carbon atom linked to the heteroatom by preference is saturated.

The term "halo" is generic to fluoro, chloro, bromo or iodo.

The term "polyhalo$C_{1-6}$alkyl" as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoro-ethyl. Preferred is trifluoromethyl. Also included are perfluoro$C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

It should be noted that different isomers of the various heterocycles may exist within the definitions as used throughout this specification and claims. For example, oxadiazole may be 1,2,4-oxadiazole, 1,3,4-oxadiazole, or 1,2,3-oxadiazole; likewise for thiadiazole, which may be 1,2,4-thiadiazole, 1,3,4-thiadiazole, or 1,2,3-thiadiazole; similarly, pyrrole may be 1H-pyrrole, or 2H-pyrrole.

It should also be noted that the radical positions on any molecular moiety used in the definitions may be anywhere on such moiety as long as it is chemically stable. For instance pyridine includes 2-pyridine, 3-pyridine and 4-pyridine; pentyl includes 1-pentyl, 2-pentyl and 3-pentyl.

When any variable (e.g. halogen or $C_{1-4}$alkyl) occurs more than one time in any constituent, each definition is independent. In particular the groups $R^1$ and $R^2$ may be absent (m or n is o), or may be present once (m or n is 1), or multiple times (m or n is 2 or 3). In the latter instance each $R^1$ or each $R^2$ can have the same or different meanings. Where $R^1$ or $R^2$ are absent, $R^1$ or $R^2$ are hydrogen. Also for the other groups that can be present multiple times, e.g. $R^4$, $R^5$, $R^6$, $R^7$, $R^8$, $R^9$, aryl, the meaning of each of these groups each time it occurs is independent from other occurances of such group.

The invention also includes the N-oxides of the compounds of formula (I), or of any of the subgroups thereof. These are compounds of formula (I) wherein one or several tertiary nitrogen atoms are oxidized to the N-oxide form. Particular N-oxides of the compounds of formula (I) are those wherein the N-oxidated nitrogen is part of an aromatic ring system.

The invention also includes the pharmaceutically acceptable addition salts, which the compounds of formula (I) or any of the subgroups thereof are able to form. These can be prepared using the appropriate acids, such as, for example, inorganic acids such as hydrohalic acids, e.g. hydrochloric or hydrobromic acid, sulfuric, hemisulphuric, nitric, phosphoric and the like acids; or organic acids such as, for example, acetic, aspartic, dodecyl-sulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids. Conversely said acid addition salt forms can be converted by treatment with an appropriate base into the free base form.

The compounds of formula (I) containing an acidic proton may also be converted into the pharmaceutically acceptable metal or amine addition base salts by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Conversely said base addition salt forms can be converted by treatment with an appropriate acid into the free acid form.

The invention also comprises the pharmaceutically acceptable solvates of the compounds of formula (I) or of any of the subgroups thereof. These comprise the hydrates and the solvent addition forms that are pharmaceutically acceptable. Examples of such forms are alcoholates, e.g. methanolates, ethanolates, propanolates, and the like.

The present compounds may also exist in their tautomeric forms. Such forms, although not explicitly indicated in the formulae in this description and claims, are intended to be included within the scope of the present invention. For example, within the definition of A, a 1,2,4-oxadiazole may be substituted with hydroxy in the 5-position, thus being in equilibrium with its respective tautomeric form as depicted below.

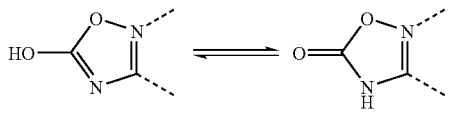

The term "stereochemically isomeric forms" as used herein, defines all possible compounds made up of the same atoms bonded by the same sequence of bonds but having different three-dimensional structures, which are not interchangeable, which the compounds of the present invention may possess. Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention, both in pure form or in a mixture with each other are intended to be embraced within the scope of the present invention, including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

The present invention is also intended to include any isotopes of atoms present in the compounds of the invention. For example, isotopes of hydrogen include tritium and deuterium and isotopes of carbon include C-13 and C-14.

Whenever used hereinabove or hereinafter, the terms "compounds of formula (I)", "the present compounds", "the compounds of the present invention" or any equivalent terms, and similarly, the terms "subgroups of compounds of formula (I)", "subgroups of the present compounds", "subgroups of the compounds of the present invention" or any equivalent terms, are meant to include the compounds of general formula (I), or subgroups of the compounds of formula (I), including the stereoisomeric forms or stereoisomeric mixtures thereof, or the pharmaceutically acceptable salts, the pharmaceutically acceptable solvates, or the N-oxides thereof.

Embodiment A comprises those compounds of formula (I) or any of the subgroups of compounds of formula (I) wherein
(1) m is 0, 1 or 2;
(1-a) m is 0 or 1; or
(1-b) m is 2.

Embodiment B comprises those compounds of formula (I) or any of the subgroups of compounds of formula (I), such as those of embodiment A, wherein
(2) A forms, together with the nitrogen and carbon atoms of the ring system to which it is attached, an aromatic heterocycle selected from pyridine, pyrimidine, pyrazine, pyridazine, triazine, imidazole, pyrazole, oxazole, isoxazole, oxadiazole, thiazole, isothiazole, and thiadiazole;
(2-a) A forms, together with the nitrogen and carbon atoms of the ring system to which it is attached, an aromatic heterocycle selected from pyridine, pyrimidine, pyrazine, pyridazine, imidazole, pyrazole, oxazole, isoxazole, oxadiazole, thiazole, isothiazole, and thiadiazole;
(2-b) A forms, together with the nitrogen and carbon atoms of the ring system to which it is attached, an aromatic heterocycle selected from pyridine, pyrimidine, pyrazine, pyridazine, imidazole, oxazole, thiazole;
(2-c) A forms, together with the nitrogen and carbon atoms of the ring system to which it is attached, an aromatic heterocycle selected from pyridine, pyrimidine, pyridazine, oxazole, thiazole;
(2-d) A forms, together with the nitrogen and carbon atoms of the ring system to which it is attached, an aromatic heterocycle selected from pyridine, pyrimidine, pyridazine, and thiazole.

Embodiment C comprises those compounds of formula (I) or any of the subgroups of compounds of formula (I), such as those of embodiments A or B, wherein
(3) each $R^1$ is, independently, a radical selected from halo, cyano, $C_{1-6}$alkyl, $—C_{1-6}$alkyl-OR$^4$, $—C(=O)—OR^4$, $—C(=O)—NR^6R^7$, $—OR^4$, $—O—C_{1-6}$alkyl-OR$^4$, —O—$C_{1-6}$alkyl-$NR^6R^7$, —O—$C_{1-6}$alkyl-O—C(=O)—$C_{1-6}$alkyl, —O—$C_{1-6}$alkyl-C(=O)—$OR^4$, —O—$C_{1-6}$alkyl-C(=O)—$NR^6R^7$, —$NR^6R^7$, —$NR^8$—C(=O)—$R^5$, —$NR^8$—C(=O)—$OR^4$, —$NR^8$—C(=O)—$NR^6R^7$, —$NR^8$—C(=O)—$C_{1-6}$alkyl-C(=O)—$OR^4$, —$NR^3$—$C_{1-6}$alkyl-$OR^4$, —$NR^8$—$C_{1-6}$alkyl-$NR^6R^7$, —$NR^8$—$C_{1-6}$alkyl-imidazolyl, —N=CH—$NR^6R^7$, —NH—C(=NH)—$NH_2$, and —O—PO($OR^8$)$_2$;

(3-a) each $R^1$ is, independently, a radical selected from $C_{1-6}$alkyl, —$C_{1-6}$alkyl-$OR^4$, —$OR^4$, —O—$C_{1-6}$alkyl-$OR^4$, —O—$C_{1-6}$alkyl-$NR^6R^7$, —O—$C_{1-6}$alkyl-C(=O)—$NR^6R^7$, —$NR^6R^7$, —$NR^8$—C(=O)—$R^5$, —$NR^8$—C(=O)—$NR^6R^7$, —$NR^3$—$C_{1-6}$alkyl-$OR^4$, —$NR^3$—$C_{1-6}$alkyl-$NR^6R^7$, —N=CH—$NR^6R^7$, —NH—C(=NH)—$NH_2$, and —O—PO($OR^8$)$_2$;

(3-b) each $R^1$ is, independently, a radical selected from $C_{1-6}$alkyl, —$C_{1-6}$alkyl-$OR^4$, —$OR^4$, —O—$C_{1-6}$alkyl-$OR^4$, —O—$C_{1-6}$alkyl-$NR^6R^7$, —$NR^6R^7$, —$NR^8$—C(=O)—$R^5$, —$NR^8$—$C_{1-6}$alkyl-$OR^4$, —$NR^8$—$C_{1-6}$alkyl-$NR^6R^7$, and —O—PO($OR^8$)$_2$;

(3-c) each $R^1$ is, independently, a radical selected from $C_{1-6}$alkyl, —$C_{1-6}$alkyl-OH, —OH, —O—$C_{1-6}$alkyl-OH, —O—$C_{1-6}$alkyl-N($R^8$)$_2$, —$NH_2$, —NH—C(=O)—H, —NH—C(=O)—$CF_3$, —$NR^8$—$C_{1-6}$alkyl-OH, —N($R^8$)—$C_{1-6}$alkyl-N($R^8$)$_2$, and —O—PO($OR^8$)$_2$;

(3-d) each $R^1$ is, independently, a radical selected from —OH, —$NH_2$, —NH—$C_{1-6}$alkyl-N($R^8$)$_2$, and —O—PO(OH)$_2$;

Embodiment D comprises those compounds of formula (I) or any of the subgroups of compounds of formula (I), such as those of embodiments A, B or C, wherein (4) n is 0, 1 or 2;
(4-a) n is 0 or 1;
(4-b) n is 0.

Embodiment E comprises those compounds of formula (I) or any of the subgroups of compounds of formula (I), such as those of embodiments A, B, C or D, wherein (5) D forms, together with the two carbon atoms of the ring system to which it is attached, an aromatic ring selected from phenyl, pyridine, pyrimidine, pyrazine, pyridazine, pyrrole, imidazole, pyrazole, furane, and thiophene;

(5-a) D forms, together with the two carbon atoms of the ring system to which it is attached, an aromatic ring selected from phenyl, pyridine, pyrimidine, pyrazine, pyrrole, imidazole, furane, and thiophene;

(5-b) D forms, together with the two carbon atoms of the ring system to which it is attached, an aromatic ring selected from phenyl, pyridine, pyrimidine, pyrrole, and thiophene;

(5-c) D forms, together with the two carbon atoms of the ring system to which it is attached, an aromatic ring selected from phenyl, pyridine, and thiophene.

Embodiment F comprises those compounds of formula (I) or any of the subgroups of compounds of formula (I), such as those of embodiments A, B, C, D or E, wherein (6) each $R^2$ is, independently, a radical selected from $C_{1-6}$alkyl, polyhalo$C_{1-6}$alkyl, halo, —$COOR^4$, —$OR^4$, and —$NR^6R^7$;

(6-a) each $R^2$ is, independently, a radical selected from $C_{1-6}$alkyl, halo, and —OR (6-b) each $R^2$ is, independently, a radical selected from $C_{1-4}$alkyl, halo, and $C_{1-4}$alkoxy;

(6-c) each $R^2$ is, independently, a radical selected from methyl, ethyl, bromo, and methoxy.

Embodiment G comprises those compounds of formula (I) or any of the subgroups of compounds of formula (I), such as those of embodiments A, B, C, D, E or F, wherein (7) $R^3$ is phenyl, pyridyl, imidazopyridyl, pyrazolopyridyl, triazolopyridyl, imidazopyrimidinyl, pyrazolopyrimidinyl; wherein said phenyl or pyridyl may optionally be substituted with 1, 2 or 3 substituents selected from $C_{1-6}$alkyl; polyhalo$C_{1-6}$alkyl; $C_{1-6}$alkyl substituted with one or two cyano or hydroxy; halo; cyano; nitro; —C(=O)—$R^5$; —C(=O)—$OR^4$; —C(=O)—$NR^6R^7$; —$OR^4$; and wherein said imidazopyridyl, pyrazolopyridyl, triazolopyridyl, imidazopyrimidinyl, pyrazolopyrimidinyl may optionally be substituted with 1 or 2 substituents selected from $C_{1-4}$alkyl, halo, amino and —$OR^4$;

(7-a) $R^3$ is phenyl, pyridyl, imidazopyridyl, imidazopyrimidinyl; wherein said phenyl or pyridyl may optionally be substituted with 1, 2 or 3 substituents selected from $C_{1-6}$alkyl; polyhalo$C_{1-6}$alkyl; $C_{1-6}$alkyl substituted with one or two cyano; halo; cyano; nitro; —C(=O)—$R^5$; —C(=O)—$OR^4$; —C(=O)—$NR^6R^7$; —$OR^4$;

(7-b) $R^3$ is phenyl, pyridyl, imidazopyridyl, imidazopyrimidinyl; wherein said phenyl or pyridyl may optionally be substituted with 1, 2 or 3 substituents selected from $C_{1-6}$alkyl; polyhalo$C_{1-6}$alkyl; $C_{1-6}$alkyl substituted with one or two cyano; halo; cyano; nitro; —C(=O)—$R^5$; —C(=O)—$OR^4$; —C(=O)—$NR^6R^7$; —OR;

(7-c) $R^3$ is phenyl, pyridyl, imidazopyridyl, imidazopyrimidinyl; wherein said phenyl or pyridyl may optionally be substituted with 1, 2 substituents selected from $C_{1-6}$alkyl; polyhalo$C_{1-6}$alkyl; $C_{1-6}$alkyl substituted with one or two cyano; halo; cyano; nitro; —C(=O)—$R^5$; —C(=O)—$OR^4$; —$OR^4$;

(7-d) $R^3$ is phenyl, pyridyl; wherein said phenyl or pyridyl, may optionally be substituted with 1 or 2 substituents selected from $C_{1-6}$alkyl; polyhalo$C_{1-6}$alkyl; $C_{1-6}$alkyl substituted with one or two cyano; halo; cyano; nitro;

(7-e) $R^3$ is phenyl, pyridyl; wherein said phenyl or pyridyl, may optionally be substituted with 1 or 2 substituents selected from $C_{1-6}$alkyl; halo; nitro;

(7-g) $R^3$ is phenyl substituted with nitro; in particular 4-nitrophenyl;

(7-h) $R^3$ is pyridyl substituted with halo; in particular 2-chloro-4-pyridyl.

Further embodiments of the present invention are those compounds of formula (I) or any of the subgroups of compounds of formula (I) wherein each $R^6$ or $R^7$ independently is hydrogen or $C_{1-4}$alkyl.

Embodiment H comprises those compounds of formula (I) or any of the subgroups of compounds of formula (I), such as those of embodiments A, B, C, D, E, F or G, wherein $R^5$ is hydrogen or $C_{1-4}$alkyl.

Embodiment I of the present invention comprises those compounds of formula (I) or any of the subgroups of compounds of formula (I), such as those of embodiments A, B, C, D, E, F, G or H, wherein $R^4$ is hydrogen or $C_{1-4}$alkyl.

Embodiment J comprises those compounds of formula (I) or any of the subgroups of compounds of formula (I), such as those of embodiments A, B, C, D, E, F, G, H or I, wherein (8) aryl is phenyl optionally substituted with 1 or 2 substituents each independently selected from $C_{1-4}$alkyl, $C_{1-4}$alkoxy, cyano, and nitro; or (8-a) aryl is phenyl substituted with 1 substituent selected from $C_{1-4}$alkyl and $C_{1-4}$alkoxy; or (8-b) aryl is phenyl.

An interesting subgroup of compounds of formula (I) comprises those compounds of the present invention that can be represented by formula:

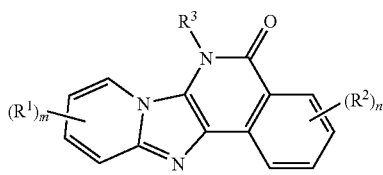

(I-a)

wherein $R^1$, $R^2$, m, n and $R^3$ are as specified in the definitions of the compounds of formula (I) or any of the subgroups thereof, and $R^3$ is as specified in the definitions of the compounds of formula (I) or any of the subgroups thereof.

Another interesting subgroup of compounds of formula (I) comprises those compounds of the present invention that can be represented by formula:

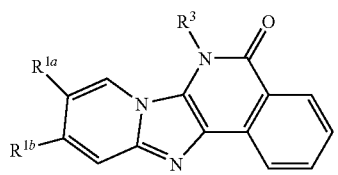

(I-b)

wherein $R^{1a}$ and $R^{1b}$ are as specified in the definitions of radical $R^1$ in the compounds of formula (I) or any of the subgroups thereof, and $R^3$ is as specified in the definitions of the compounds of formula (I) or any of the subgroups thereof.

Another interesting subgroup of compounds of formula (I) comprises those compounds, which may be represented by formula:

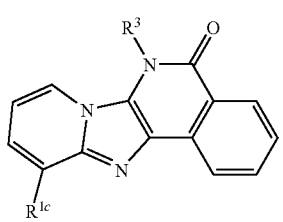

(I-c)

wherein $R^{1c}$ is as specified in the definitions of radical $R^1$ in the compounds of formula (I) or any of the subgroups thereof, and $R^3$ is as specified in the definitions of the compounds of formula (I) or any of the subgroups thereof.

Other interesting subgroups of compounds of formula (I) comprises those compounds of the present invention that may be represented by formulae:

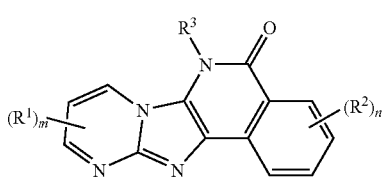

(I-d)

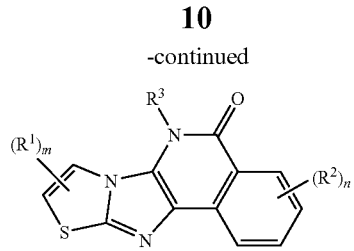

(I-e)

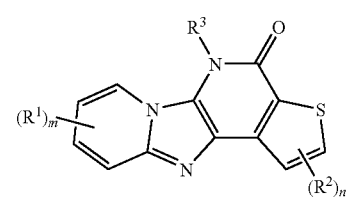

(I-f)

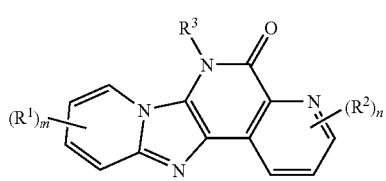

(I-g)

wherein $R^1$, $R^2$, $R^3$, m, and n are as specified in the definitions of the compounds of formula (I) or any of the subgroups thereof.

Yet another interesting subgroup of compounds of formula (I) comprises those compounds of the present invention that may be represented by formula:

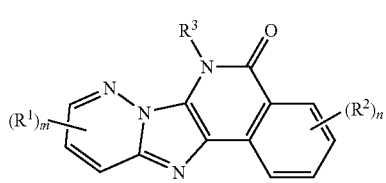

(I-h)

wherein $R^1$, $R^2$, $R^3$, m, and n are as specified in the definitions of the compounds of formula (I) or any of the subgroups thereof, in particular those represented by formula

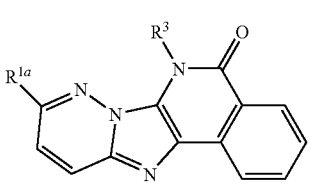

(I-h-1)

wherein $R^{1a}$ is as specified in the definitions of radical $R^1$ in the compounds of formula (I) or any of the subgroups thereof, and $R^3$ is as specified in the definitions of the compounds of formula (I) or any of the subgroups thereof.

Interesting subgroups of compounds are those of formulae (I-a), (I-c), (I-d), (I-e), (I-f), (I-g), (I-h) or (I-h-1) wherein n is 0, i.e. wherein $R^2$ is hydrogen.

A particular subgroup of compounds of the invention are those compounds of formula (I) or any of the subgroups specified herein, wherein the compound of formula (I) is present as an acid-addition salt form, wherein the salt preferably is selected from trifluoroacetate, fumarate, methanesulfonate, oxalate, acetate and citrate.

Compounds of interest are compounds number 1, 10, 76, 82, 88, 110, 122 and 188, in particular compound I, as listed in tables 1-4 following the experimental part, and the salts and possible stereoisomers thereof.

The compounds of the present invention show antiretroviral activity, in particular they are active against HIV. In particular, the compounds of formula (I) are inhibitors of the HIV reverse transcriptase. In general, the compounds of the present invention have a good selectivity as measured by the ratio between $EC_{50}$ and $CC_{50}$, showing good activity against resistant mutant strains, even against multi-drug resistant strains. Currently used HIV reverse transcriptase ("RT") inhibitors lose effectivity due to mutations, which cause changes in the RT enzyme. This results in a less effective interaction of the inhibitor with the RT enzyme, whereby the virus becomes less "sensitive" to the RT inhibitor. Mutants where the RT inhibitor no longer is effective are referred to as "resistant mutants". "Multi-drug resistance" is where the mutants are resistant to multiple other HIV RT inhibitors. The resistance of a mutant to a particular HIV RT inhibitor is expressed by the ratio of the $EC_{50}$ of the HIV RT inhibitor measured with mutant HIV RT to the $EC_{50}$ of the same HIV RT inhibitor measured with wild type HIV RT. This ratio is also referred to as "fold change" in resistance (FR).

Many of the mutants occurring in the clinic have a fold resistance of 100 or more against the commercially available HIV NNRTIs, like nevirapine, efavirenz, delavirdine. Clinically relevant mutants of the HIV reverse transcriptase enzyme may be characterized by a mutation at codon position 100, 103 and 181. As used herein a codon position means a position of an amino acid in a protein sequence. Mutations at positions 100, 103 and 181 relate to non-nucleoside RT inhibitors.

Of interest are those compounds of formula (I) having a fold resistance ranging between 0.01 and 100, in particular between 0.1 and 30, more in particular between 0.1 and 20, or further in particular between 0.1 and 10, against at least one mutant HIV reverse transcriptase. Of interest are those compounds of formula (I) having a fold resistance in the range of 0.01 to 100, in particular between 0.1 and 30, more in particular between 0.1 and 20, or further in particular between 0.1 and 10, against HIV species having at least one or at least two mutation(s) in the amino acid sequence of HIV reverse transcriptase as compared to the wild type sequence at a position selected from 100, 103 and 181.

In general, compounds of formula (I) are active against mutant strains that show resistance toward currently available NNRTIs such as nevirapine, efavirenz, delavirdine.

The compounds of the invention interact through a unique mechanism of action in that they are competitive RT inhibitors and moreover show increased activity when co-administered with a nucleoside phosphate such as ATP. Therefore the compounds of the invention may find use in HIV drug combinations, in particular in combinations containing one, two or more HIV inhibiting agents.

The compounds of the invention may be used to treat other diseases that emerge because of HIV infection, which include thrombocytopaenia, Kaposi's sarcoma and infection of the central nervous system characterized by progressive demyelination, resulting in dementia and symptoms such as, progressive dysarthria, ataxia and disorientation. Still other diseases that have been associated with and that may be treated using the compounds of this invention comprise peripheral neuropathy, progressive generalized lymphadenopathy (PGL) and AIDS-related complex (ARC).

In a further aspect, the present invention concerns a compound of formula (I) or of any subgroup thereof, for use as a medicine, in particular against the above-mentioned diseases, or in the prophylaxis thereof. In another aspect, the present invention concerns the use of a compound of formula (I) or of any subgroup thereof, for the manufacture of a medicament for preventing, treating or combating HIV infection or a disease associated with HIV infection. Or, the present invention concerns the use of a compound of formula (I) or of any subgroup thereof, for the manufacture of a medicament useful for inhibiting replication of HIV, in particular of HIV having a mutant HIV reverse transcriptase, more in particular a multi-drug resistant mutant HIV reverse transcriptase. Or, the present invention relates to the use of a compound of formula (I) or of any subgroup thereof in the manufacture of a medicament useful for preventing, treating or combating a disease associated with HIV infection wherein the reverse transcriptase of the HIV virus is mutant, in particular a multi-drug resistant mutant HIV reverse transcriptase.

The invention further relates to a method for preventing, treating or combating HIV infection or a disease associated with HIV infection in a human, comprising administering to said human an effective amount of a compound of formula (I) or of any subgroup thereof. In another aspect, the invention concerns a method for preventing, treating or combating infection or disease associated with infection of a human infected with a mutant HIV virus, or with a multi drug-resistant HIV virus, comprising administering to said human an effective amount of a compound of formula (I) or of any subgroup thereof.

In yet another aspect, the invention relates to a method for inhibiting replication of a HIV virus, in particular a HIV virus having a mutant HIV reverse transcriptase, more in particular a multi-drug resistant mutant HIV reverse transcriptase in a human infected therewith, said method comprising administering to a human in need thereof an effective amount of a compound of formula (I) or any subgroup thereof.

Said use as a medicine or method of treatment comprises the systemic administration to HIV-infected subjects of an amount effective to combat the conditions associated with HIV infection.

The compounds of the present invention may also find use in inhibiting HIV in ex vivo samples containing HIV or expected to be exposed to HIV. Hence, the present compounds may be used to inhibit HIV present in a body fluid sample that contains or is suspected to contain or be exposed to HIV.

A number of synthesis procedures to prepare compounds of the present invention are described below. In these procedures, the reaction products may be isolated and, if necessary, further purified according to methodologies generally known in the art such as, for example, extraction, crystallization, trituration and chromatography.

The compounds of formula (I) can be prepared as outlined in the following scheme. In this scheme, R¹, R², R³ and X are as defined above.

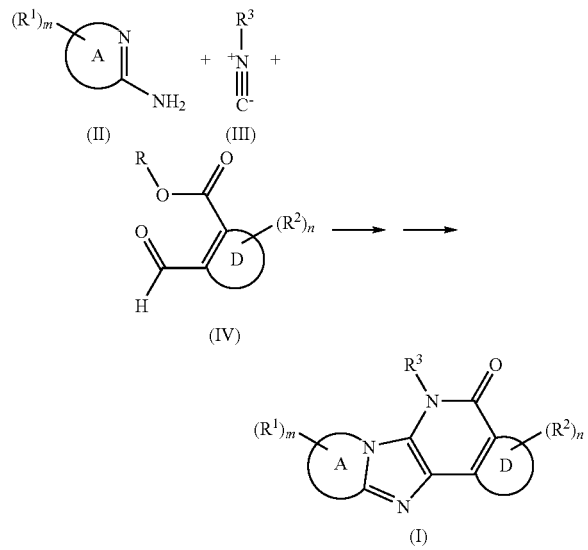

The cyclic amine (II) is condensed with an isocyanide (III) and a cyclic aldehyde ester (IV) in a cyclization reaction to yield end product (I). This reaction is preferably conducted as a two-step procedure. In the first step, starting materials (II), (III) and (IV) are condensed, in particular in a tricomponent Ugi reaction, wherein it is assumed that a bicyclic derivative (IV-a) is formed, which is cyclized in the second step:

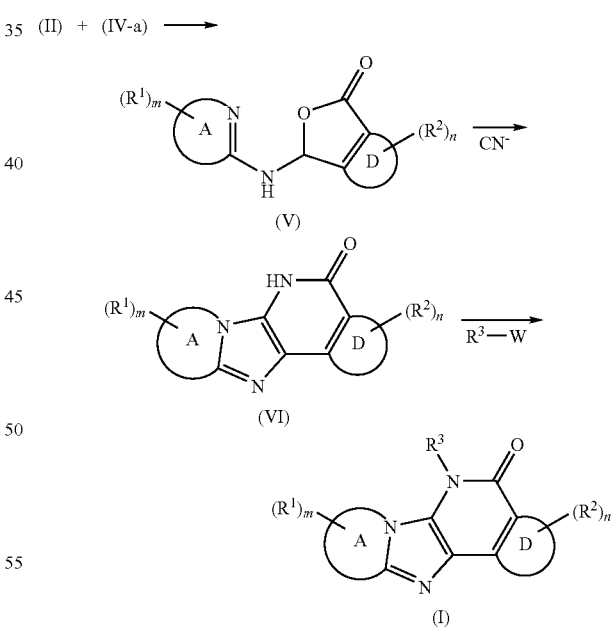

In the first step the starting materials (II), (III), and (IV) are reacted in the presence of a strong acid such as a hydrohalic acid, in particular hydrochloric or hydrobromic acid, perchloric acid, sulfuric acid, trifluoroacetic acid and the like. In the second step further cyclization of the assumed intermediate (IV-a) to compounds (I) takes place. The second step is conducted in the presence of a strong base such as an alkoxide, in particular an alkali metal alkoxide, e.g. sodium or potassium methoxide, ethoxide, isopropyloxide, t.butoxide and the like, or a trialkylamine such as triethylamine, a carbonate such as sodium or potassium carbonate, a hydrogen carbonate such as sodium or potassium hydrogen carbonate, a hydride such as sodium or potassium hydride. In intermediates (IV) and (IV-a), the group —COOR is an ester derived from a suitable alcohol, in particular from a $C_{1-6}$alkanol such as methanol, ethanol, and the like. Preferably R is a methyl group. The two steps may be conducted in different solvents but preferably the same solvent is used. Suitable solvents for this reaction comprise, for example, alcohols, such as the lower alkanols, in particular methanol, ethanol, n.propanol, isopropanol; halogenated hydrocarbons such as dichloromethane or chloroform; ethers such as tertrahydrofuran, dioxan; dipolar aprotic solvents such as DMA, DMF, DMSO, acetonitrile; and the like solvents.

It may be desirable to protect the groups R¹ and/or R² and to remove the protecting groups after the cyclization reaction. This may be recommendable where R¹ and/or R² are hydroxy or a hydroxy substituted group, or amino or an amino substituted group. Suitable protecting groups for amino comprise benzyl, benzyloxycarbonyl, t-butyloxy-carbonyl; suitable protecting groups for hydroxy comprise benzyl, t.butyl, or ester or amide groups. The protecting groups can be removed by hydrolysis with acid or base or by catalytic hydrogenation.

In an alternative synthesis route, the aromatic amine and a compound of formula (IV-a) which is a compound (IV) wherein R is H are condensed to an intermediate (V), which is reacted with a metal cyanide such as alkali metal cyanide, e.g. KCN, to yield the tetracyclic compounds (VI). The latter are arylated with a reagent R³—W wherein R³ is as specified above and W is an appropriate leaving group such as a halo group, in particular chloro or bromo. In the latter case, a catalyst such as copper(I) iodide may be added. Usually the reaction is conducted in a suitable solvent, e.g. DMF, DMA, dichloromethane, in the presence of a base. In particular instances heterocycles with special groups such as boronic acid (i.e. W is —B(OH)₂) or borate esters (i.e. W is —B(OR)₂ wherein R is alkyl or alkylene, e.g. R is methyl, ethyl or ethylene) can be used, the reaction being typically conducted in the presence of a copper salt, in particular copper(II) acetate, and a suitable quencher like pyridine may be added to the reaction mixture.

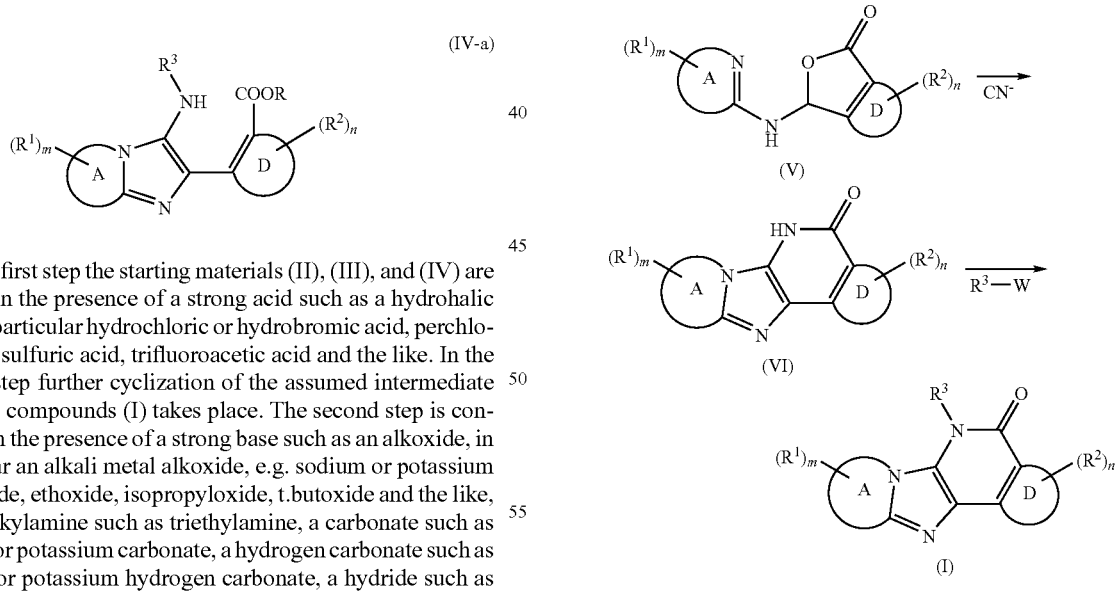

The compounds of formula (I) may be transferred into other compounds of formula (I) with different substitution using art-known transformation techniques. For instance, the compounds of formula (I) having an aromatic substituent, which is nitro may be reduced to the corresponding amino analogs, which in turn may be further derivatized.

Compounds of formula (I) wherein R³ is an aromatic moiety substituted with halo can be converted to the corresponding cyano compounds by reacting the starting materials with a suitable cyano nucleophile, e.g. copper(I) cyanide. Compounds of formula (I) wherein $R^1$ or $R^2$ are hydroxy or amino can be alkylated using appropriate alkylating agents. Compounds of formula (I) wherein $R^1$ is hydroxy can be converted to the corresponding compounds wherein $R^1$ is —O—PO—$(OH)_2$ by reaction with a dialkyl phosphoramidite, oxidation of the formed dialkylphosphite to the corresponding dialkylphosphate, e.g. with a peroxide, and removal of the alkyl groups, e.g. with acid.

The compounds of formula (I) may also be converted to the corresponding N-oxide forms following art-known procedures for converting a tri-substituted nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials used in the preparation of the compounds of formula (I) are either known compounds or analogs thereof, which either are commercially available or can be prepared by art-known methods.

The compounds of this invention can be used as such but preferably are used in the form of pharmaceutical compositions. Thus in a further aspect, the present invention relates to pharmaceutical compositions that as active ingredient contain an effective dose of a compounds of formula (I) in addition to a carrier which may comprise customary pharmaceutically innocuous excipients and auxiliaries. The pharmaceutical compositions normally contain 0.1 to 90% by weight of a compound of formula (I). The pharmaceutical compositions can be prepared in a manner known per se to one of skill in the art. To this purpose, a compound of formula (I), together with one or more solid or liquid carrier which may comprise pharmaceutical excipients and/or auxiliaries and, if desired, in combination with other pharmaceutical active compounds, are converted into a suitable administration form or dosage form.

Pharmaceuticals that contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries that are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126, 443), AVX 754 ((-)-dOTC), fozivudine tidoxil (FZT), phosphazide, HDP-990003, KP-1461, MIV-210, racivir (PSI-5004), UC-781 and the like; non-nucleoside reverse transcriptase inhibitors (NNRTIs) such as delavirdine (DLV), efavirenz (EFV), nevirapine (NVP), dapivirine (TMC120), etravirine (TMC125), rilpivirine (TMC278), DPC-082, (+)-Calanolide A, BILR-355, and the like; nucleotide reverse transcriptase inhibitors (NtRTIs), e.g. tenofovir ((R)-PMPA) and tenofovir disoproxil fumarate (TDF), and the like; nucleotide-competing reverse transcriptase inhibitors (NcRTIs), such as the compounds described in WO2004/046143; inhibitors of trans-activating proteins, such as TAT-inhibitors, e.g. RO-5-3335, BI-201, and the like; REV inhibitors; protease inhibitors e.g. ritonavir (RTV), saquinavir (SQV), lopinavir (ABT-378 or LPV), indinavir (IDV), amprenavir (VX-478), TMC126, nelfinavir (AG-1343), atazanavir (BMS 232, 632), darunavir (TMC114), fosamprenavir (GW433908 or VX-175), brecanavir (GW-640385, VX-385), P-1946, PL-337, PL-100, tipranavir (PNU-140690), AG-1859, AG-1776, Ro-0334649 and the like; entry inhibitors which comprise fusion inhibitors (e.g. enfuvirtide (T-20)), attachment inhibitors and co-receptor inhibitors, the latter comprise the CCR5 antagonists (e.g. ancriviroc, CCR5 mAb004, maraviroc (UK-427,857), PRO-140, TAK-220, TAK-652, vicriviroc (SCH-D, SCH-417,690)) and CXR4 antagonists (e.g. AMD-070, KRH-27315), examples of entry inhibitors are PRO-542, TNX-355, BMS-488,043, BlockAide/CR™, FP 21399, hNMOI, nonakine, VGV-1; a maturation inhibitor for example is PA-457; inhibitors of the viral integrase e.g. MK-0518, JTK-303 (GS-9137), BMS-538,158; ribozymes; immunomodulators; monoclonal antibodies; gene therapy; vaccines; siRNAs; antisense RNAs; microbicides; Zinc-finger inhibitors.

The compounds of the present invention may also be administered in combination with immunomodulators (e.g., bropirimine, anti-human alpha interferon antibody, IL-2, methionine enkephalin, interferon alpha, and naltrexone) with antibiotics (e.g., pentamidine isothiorate) cytokines (e.g. Th2), modulators of cytokines, chemokines or modulators of chemokines, chemokine receptors (e.g. CCR5, CXCR4), modulators chemokine receptors, or hormones (e.g. growth hormone) to ameliorate, combat, or eliminate HIV infection and its symptoms. Such combination therapy in different formulations, may be administered simultaneously, sequentially or independently of each other. Alternatively, such combination may be administered as a single formulation, whereby the active ingredients are released from the formulation simultaneously or separately.

The compounds of the present invention may also be administered in combination with modulators of the metabolization following application of the drug to an individual. These modulators include compounds that interfere with the metabolization at cytochromes, such as cytochrome P450. It is known that several isoenzymes exist of cytochrome P450, one of which is cytochrome P450 3A4. Ritonavir is an example of a modulator of metabolization via cytochrome P450. Such combination therapy in different formulations, may be administered simultaneously, sequentially or independently of each other. Alternatively, such combination may be administered as a single formulation, whereby the active ingredients are released from the formulation simultaneously or separately. Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with substances such as solubilizers, emulsifiers or other auxiliaries, are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or mixtures thereof.

Suitable pharmaceutical formulations for administration in the form of aerosols or sprays are, for example, solutions, suspensions or emulsions of the compounds of the invention in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ α-, β- or γ-cyclo-dextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility. Appropriate cyclodextrins are α-, β- or γ-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyl-ethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavours.

Other convenient ways to enhance the solubility of the compounds of the present invention in pharmaceutical compositions are described in WO 94/05263, WO 98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bio-available to the organisms to which they are administered.

The term "a solid dispersion" also comprises dispersions, which are less homogeneous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide, which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those that physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The compounds of the present invention may be incorporated in hydrophilic polymers and this mixture may be applied as a coat film on small beads. In one embodiment, these beads comprise a central, rounded or spherical core, a coating film of a hydrophilic polymer and an antiretroviral agent and a seal-coating polymer layer. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof. The thus obtained coated beads have a good bioavailability and are suitable for preparing oral dosage forms.

The dose of the compounds of this invention to be administered depends on the individual case and, as customary, is to be adapted to the conditions of the individual case for an optimum effect. Thus it depends on the frequency of administration and on the potency and duration of action of the compounds employed in each case for therapy or prophylaxis, but also on the nature and severity of the infection and symptoms, and on the sex, age, weight co-medication and individual responsiveness of the human or animal to be treated and on whether the therapy is acute or prophylactic. Customarily, the daily dose of a compound of formula (I) in the case of administration to a patient approximately 75 kg in weight is 1 mg to 3 g, preferably 3 mg to 1 g, more preferably, 5 mg to 0.5 g. The dose can be administered in the form of an individual dose, or divided into several, e.g. two, three, or four, individual doses.

EXAMPLES

The following examples illustrate compounds of formula (I), the preparation and pharmacological properties thereof, and should not be construed as a limitation of the scope of the present invention.

Hereinafter, "DMSO" is defined as dimethylsulfoxide, "DMF" is defined as N,N-dimethylformamide and "THF" is defined as tetrahydrofuran.

Example 1

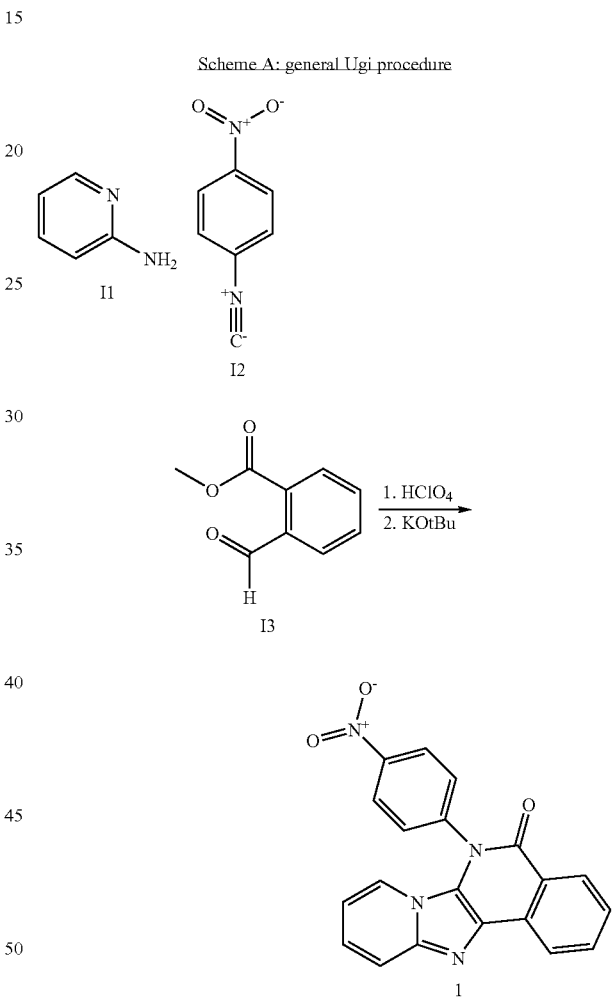

A mixture of 2-aminopyridine (I1) (1.0 equiv., 5.30 mmol, 0.500 g), 4-nitrophenyl isocyanide (I2) (1.1 equiv., 5.80 mmol, 0.870 g), methyl 2-formylbenzoate (I3) (1.1 equiv., 5.80 mmol, 0.960 g) and perchloric acid (0.1 equiv., 0.53 mmol, 0.053 g) in methanol (25 ml) was stirred at room temperature until no starting material was left. The progress of the reaction was monitored by LCMS. Potassium tert-butoxide (1.1 equiv., 5.80 mmol, 0.660 g) was added and the reaction mixture was further stirred at room temperature for 2 h. The resulting precipitate was filtered off and washed with isopropanol and isopropyl ether to give 6-(4-nitrophenyl)-pyrido[2',1':2,3]imidazo-[4,5-c]isoquinolin-5(6H)-one (1) (1.20 g, yield=63%, purity (LC)=95%).

Example 2

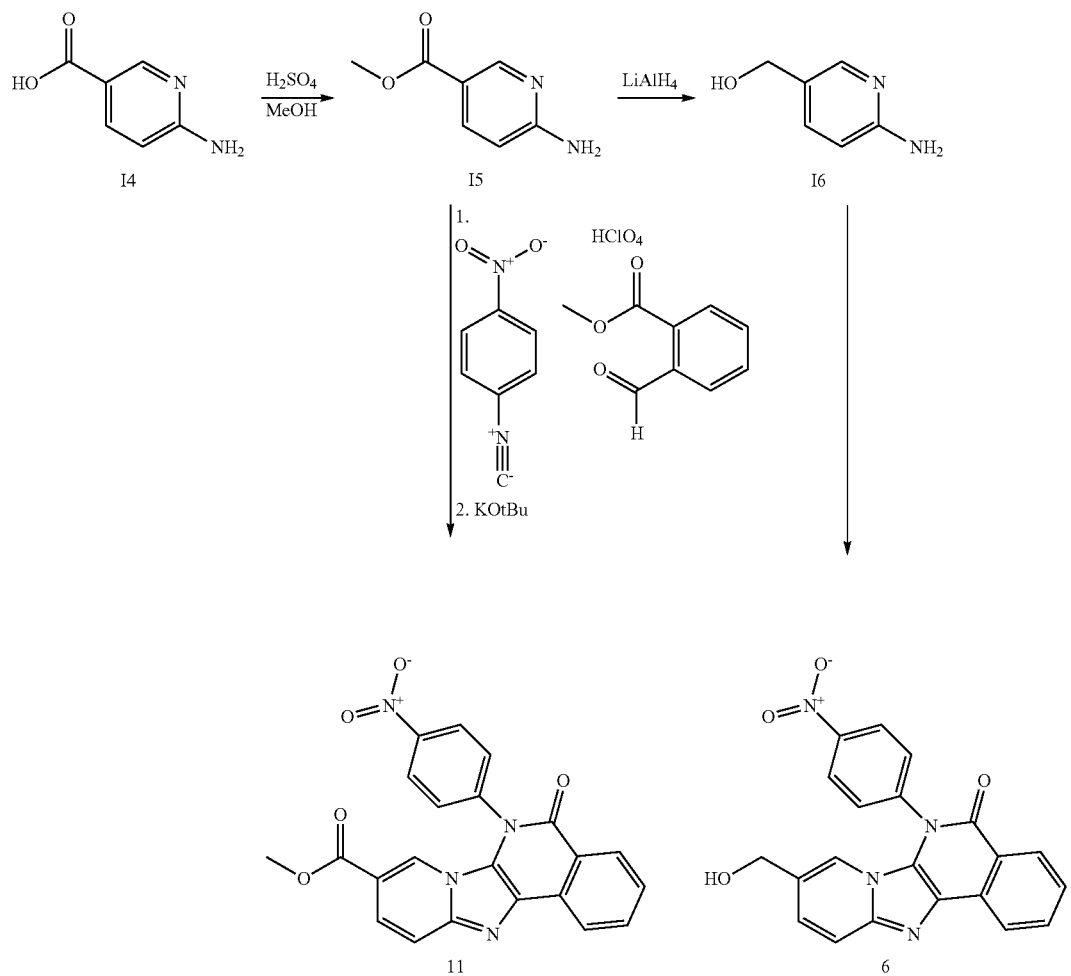

Scheme A1

A mixture of 6-aminonicotinic acid (1.0 equiv., 7.24 mmol, 1.00 g) and sulfuric acid (6.00 equiv., 65.16 mmol, 6.39 g) in methanol was refluxed for 24 h. After cooling to room temperature, the reaction mixture was concentrated under reduced pressure and then made alkaline by the addition of a saturated aqueous NaHCO$_3$ solution. The aqueous layer was extracted with ethyl acetate, the combined organic layers were dried with MgSO$_4$ and concentrated in vacuo to give methyl 6-amino-pyridine-3-carboxylate (15) (0.70 g, yield=64%) as a white crystalline product.

Compound 11 was prepared according to the general Ugi procedure, as described in example 1. To this end, a mixture of I5 (1.0 equiv., 0.85 mmol, 0.130 g), 4-nitrophenyl isocyanide (1.1 equiv., 0.94 mmol, 0.139 g), methyl 2-formylbenzoate (1.1 equiv., 0.94 mmol, 0.154 g) and perchloric acid (0.2 equiv., 0.17 mmol, 0.017 g) in methanol (5 ml) was stirred at 40° C. overnight. After cooling to room temperature, potassium tert-butoxide (1.2 equiv., 1.02 mmol, 0.114 g) was added and the reaction mixture was further stirred at room temperature for 2 h. The resulting precipitate was filtered off and successively washed with isopropanol and isopropyl ether to give methyl 5,6-dihydro-6-(4-nitrophenyl)-5-oxo-pyrido[2',1':2,3]imidazo[4,5-c]isoquinolin-9-carboxylate (11) (0.094 g, yield=27%, purity (LC)=99%).

Compound I5 (1.0 equiv., 3.94 mmol, 0.600 g) was added portion wise to a suspension of LiAlH$_4$ (3.00 equiv., 11.83 mmol, 0.449 g) in dry THF (17 ml) at 0° C. The reaction mixture was stirred at room temperature overnight. Excess LiAlH$_4$ was destroyed by addition of methanol (while cooling on ice), the reaction mixture was filtered over Celite and the filtrate concentrated under reduced pressure. The crude product was purified by column chromatography (dichloromethane/methanol 75:25) to give 6-amino-3-pyridinemethanol (16) (0.330 g, yield=67%) as a white solid. $^1$H NMR (6, CD$_3$OD): 4.43 (2H, s), 6.58 (1H, d, J=8.5 Hz), 7.48 (1H, dd, J=8.5, 2 Hz) 7.86 (1H, d, J≈2 Hz)

9-Hydroxymethyl-6-(4-nitrophenyl)-pyrido[2',1':2,3]imidazo[4,5-c]isoquinolin-5(6H)-one (6) was prepared using the Ugi procedure as described for 11 (yield=66%, purity (LC) =98%).

Example 3

Scheme A2

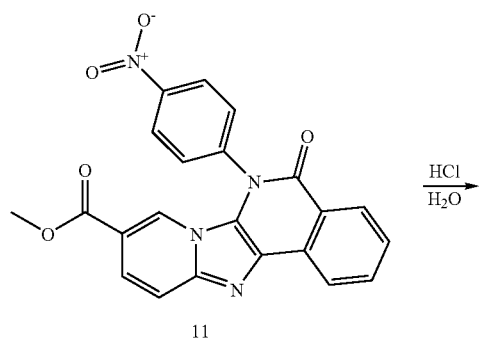

11

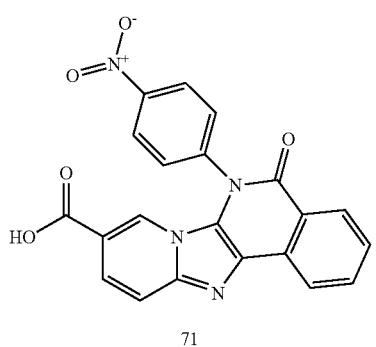

71

A suspension of compound 11 (1.0 equiv., 0.060 mmol, 0.025 g) in a concentrated aqueous HCl solution (1 ml) was stirred at 60° C. overnight. The solvent was concentrated under reduced pressure to give the hydrochloride salt of 5,6-dihydro-6-(4-nitrophenyl)-5-oxo-pyrido[2',1':2,3]imidazo[4,5-c]isoquinolin-9-carboxylic acid (71), which was further dried under high vacuum (0.024 g, yield=91%, purity (LC) =98%).

Example 4

Scheme A3

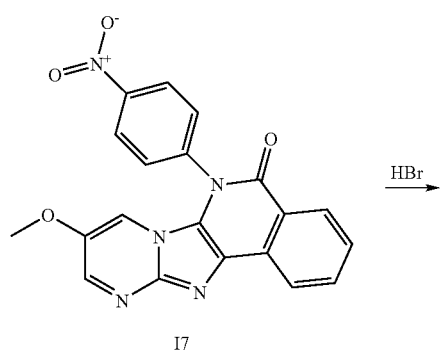

I7

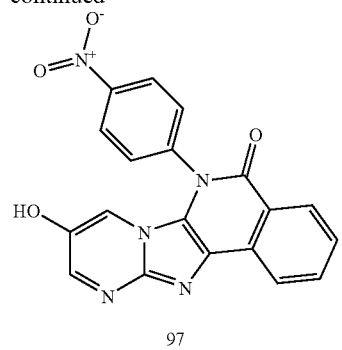

97

A suspension of 9-methoxy-6-(4-nitrophenyl)-pyrimido[2',1':2,3]imidazo[4,5-c]-isoquinolin-5(6H)-one (17) (0.26 mmol, 0.100 g) in a concentrated aqueous HBr solution (5 ml) was refluxed overnight. The reaction mixture was evaporated under reduced pressure. The crude product was brought on a filter and washed with methanol, isopropanol and isopropylether successively to give the hydrobromide salt of 9-hydroxy-6-(4-nitrophenyl)-pyrimido[2',1':2,3]imidazo[4,5-c]isoquinolin-5(6H)-one (97) (0.025 g, yield=8%, purity (LC) =90%).

Example 5

Scheme A4

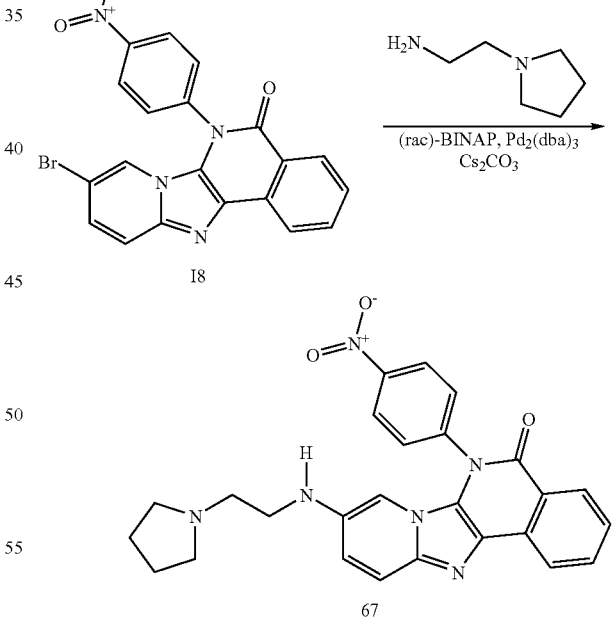

An oven-dried pyrex screw-tube was charged with rac-2,2'-bis(diphenylphosphino)-1,1'-binaphthyl ((rac)-BINAP) (0.3 equiv., 0.138 mmol, 0.086 g), Pd₂(dibenzylidene-acetone)₃ (Pd₂ dba₃) (0.1 equiv., 0.046 mmol, 0.042 g) and Cs₂CO₃ (1.4 equiv., 0.643 mmol, 0.210 g). Dry dioxane (1 ml) was added and the screw-tube was purged with Ar. The reaction mixture was heated at 80° C. for 30 min, after which it was allowed to cool to room temperature. 9-Bromo-6-(4- nitrophenyl)-pyrido[2',1':2,3]-imidazo[4,5-c]isoquinolin-5 (6H)-one (18) (1.0 equiv., 0.460 mmol, 0.200 g) and pyrrolidineethanamine (1.0 equiv., 0.460 mmol, 0.052 g) were added and the reaction mixture was stirred at 100° C. until no starting materials were left. The progress of the reaction was monitored by LCMS. Removal of the solvent under reduced pressure, followed by column chromatography (gradient elution: dichloromethane→dichloromethane/methanol 9:1) of the resulting residue gave 6-(4-nitrophenyl)-9-(2-pyrrolidin-1-yl-ethylamino)-pyrido[2',1':2,3]imidazo[4,5-c]isoquinolin-5(6H)-one (67) (0.055 g, yield=26%, purity (LC)=97%).

Example 6

Scheme A5

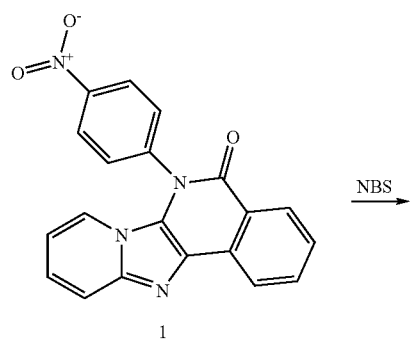

1

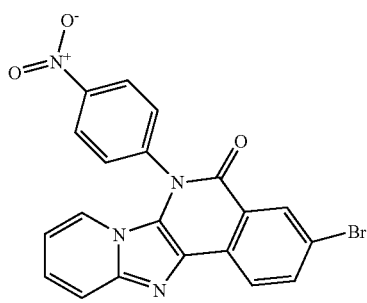

101

N-Bromosuccinimide (1.2 equiv., 0.358 mmol, 0.061 g) was added to a solution of 1 (1.0 equiv., 0.295 mmol, 0.105 g) in DMF (3 ml). The reaction mixture was stirred at room temperature for 4 h. Water was added, the resulting precipitate was isolated by filtration and washed with water, isopropanol and isopropyl ether successively to give 3-bromo-6-(4-nitrophenyl)-pyrido[2',1':2,3]imidazo[4,5-c]isoquinolin-5(6H)-one (101) (0.050 g, yield=36%, purity (LC)=93%).

Example 7

Scheme A6

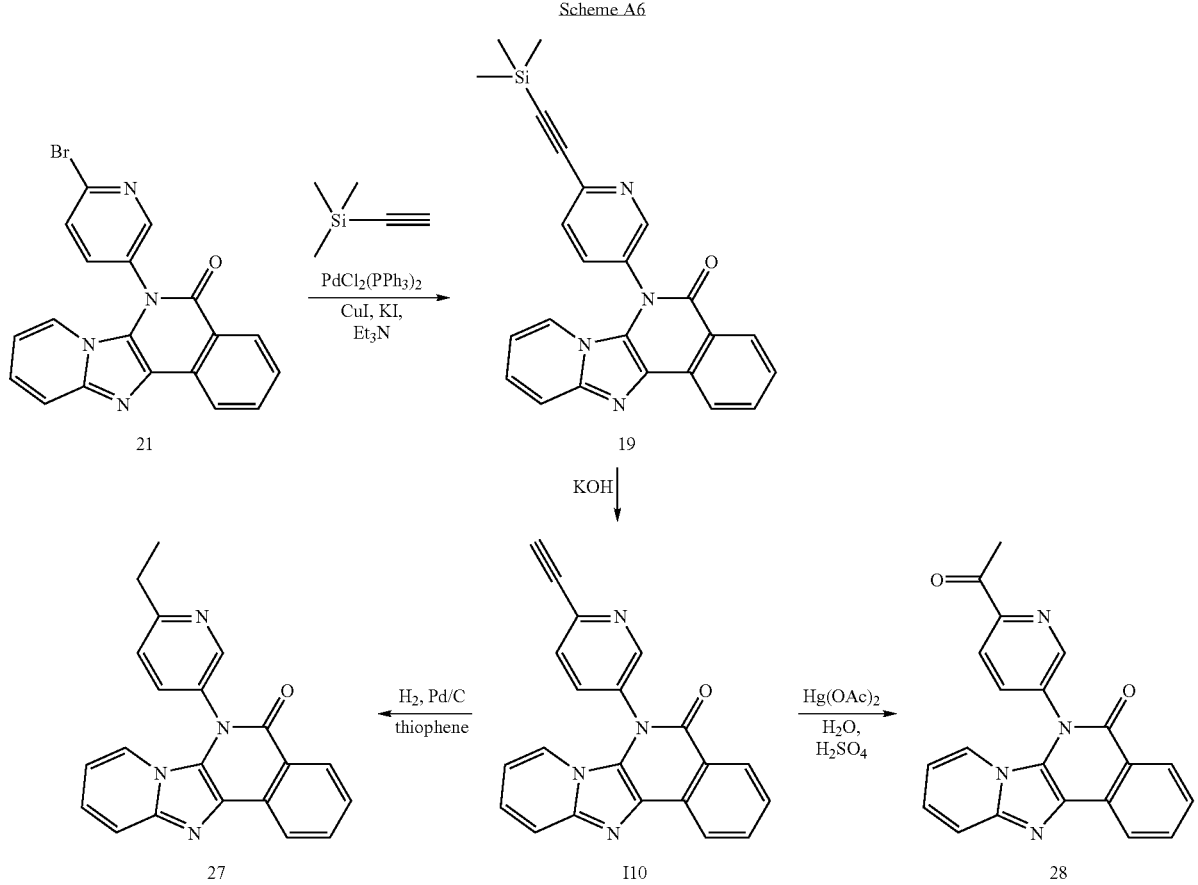

CuI (0.2 equiv., 0.256 mmol, 0.049 g), dichlorobis(triphenylphosphine)-palladium(II) (0.1 equiv., 0.13 mmol, 0.090 g), triethylamine (1.0 equiv., 1.28 mmol, 0.129 g), (trimethylsilyl)acetylene (10.0 equiv., 12.8 mmol, 1.26 g) and KI (10.0 equiv., 12.8 mmol, 2.12 g) were added to a mixture of 6-(6-bromo-pyridin-3-yl)-pyrido-[2',1':2,3]imidazo[4,5-c]isoquinolin-5(6H)-one (21) (1.0 equiv., 1.28 mmol, 0.50 g) in dry DMF (10 ml). The reaction mixture was stirred at room temperature under $N_2$ atmosphere for 24 h. After addition of a second portion of CuI (0.20 equiv., 0.256 mmol, 0.049 g) and dichlorobis(triphenylphosphine)-palladium(II) (0.1 equiv., 0.13 mmol, 0.090 g), the reaction mixture was further stirred at 60° C. for 17 h. The solvent was evaporated under reduced pressure and the pasty residue was mixed with dichloromethane and washed with water. The organic layer was evaporated under reduced pressure and the residue purified by column chromatography (ethyl acetate/heptane 60:40) to afford 6-[6-[(trimethylsilanyl)ethynyl]-pyridin-3-yl]-pyrido[2',1':2,3]-imidazo[4,5-c]isoquinolin-5(6H)-one (I9) (0.50 g, yield=96%, purity (LC)=95%).

KOH (1.1 equiv., 0.565 mmol, 0.032 g) was added to a mixture of compound I9 (0.514 mmol, 0.210 g) in methanol (50 ml). The reaction mixture was stirred at room temperature under $N_2$ atmosphere for 1 h. A 0.5 M aqueous solution of HCl (1.1 equiv., 0.565 mmol, 1.13 ml) was added, and the resulting mixture was stirred at room temperature for 10 min. The solvent was evaporated under reduced pressure and the residue was purified by column chromatography (ethyl acetate/dichloromethane 60:40) to give 6-(6-ethynyl-pyridin-3-yl)-pyrido[2',1':2,3]imidazo[4,5-c]isoquinolin-5(6H)-one (I10) (0.150 g, yield=87%).

A solution of compound I10 (1.0 equiv., 0.22 mmol, 73 mg) in acetone/water (8:2, 2 ml) was added to a mixture of mercury(II) acetate (1.0 equiv., 0.22 mmol, 69 mg) and sulphuric acid (2.0 equiv., 0.43 mmol, 43.0 mg) in acetone/water (8:2, 2 ml) at 40° C. The reaction mixture was heated at reflux for 4 h. The solvent was evaporated under reduced pressure to almost dryness, a saturated aqueous $K_2CO_3$ solution was added and the water phase was extracted with dichloromethane. The organic phase was dried with $MgSO_4$ and evaporated under reduced pressure. The residue was purified over silica gel (ethyl acetate/dichloromethane 25:75) to give 6-[6-(1-oxyethyl)-pyridin-3-yl]-pyrido[2',1':2,3]imidazo[4,5-c]isoquinolin-5(6H)-one (28) (38 mg, yield=49%, purity (LC)=99%).

Palladium/carbon (0.050 g, 10% w/w Pd/C) and thiophene (1.2 equiv., 0.096 mmol, 0.20 ml 4% in isopropylether) were added to a solution of compound I10 (1.0 equiv., 0.08 mmol, 27 mg) in methanol (150 ml). The reaction mixture was stirred under $H_2$ at room temperature for 10 min. The filtered reaction mixture was evaporated under reduced pressure, affording 6-(6-ethyl-pyridin-3-yl)-pyrido[2',1':2,3]imidazo[4,5-c]-isoquinolin-5(6H)-one (27) (12.2 mg, yield=45%, purity (LC)=100%).

Example 8

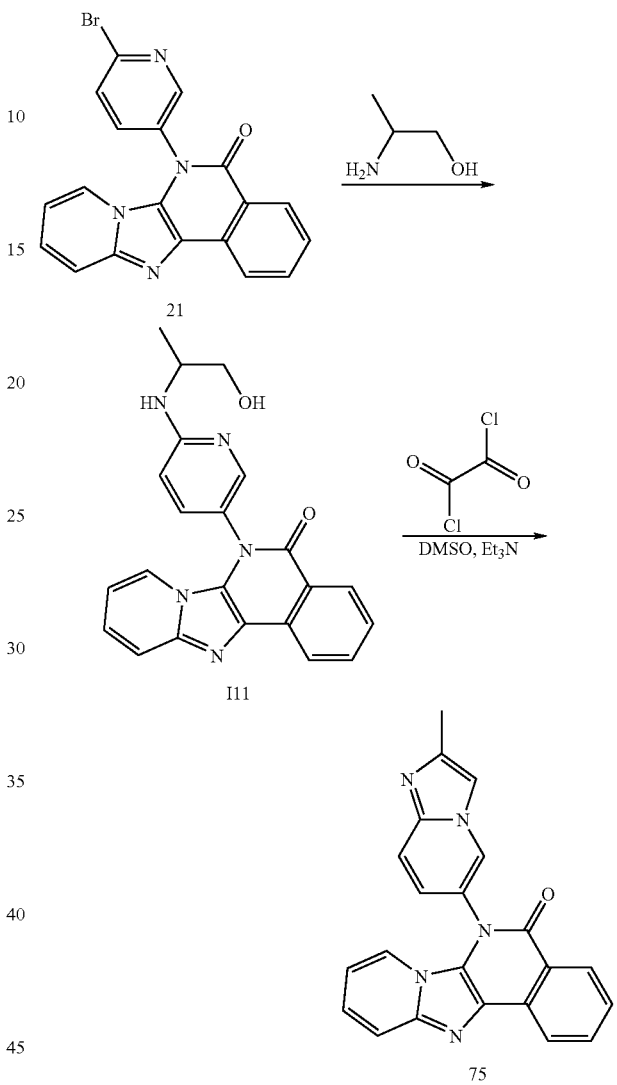

Scheme A7

A mixture of compound 21 (1.0 equiv., 0.583 mmol, 0.228 g) and 2-amino-1-propanol (1.5 ml) was stirred for 50 min under microwave irradiation (microwave settings: temperature=180° C., maximum pressure=17 bar, maximum power=200 W). The reaction mixture was mixed with water (10 ml) and stirred at room temperature for 5 min. The resulting precipitate was filtered off and subsequently washed with water and tetrahydrofuran to afford 6-[6-[(2-hydroxy-1-methyl-ethyl)amino]-pyridin-3-yl]-pyrido[2',1':2,3]imidazo[4,5-c]isoquinolin-5(6H)-one (I11) (0.150 g, yield=67%, purity (LC)=96%).

A mixture of DMSO (2.1 equiv., 0.812 mmol, 0.063 g) and dichloromethane (1.5 ml) was cooled to −78° C. under $N_2$ atmosphere in a dry sealed tube. A solution of oxalyl chloride (2.0 equiv., 0.773 mmol, 0.098 g) in dichloromethane (1.0 ml) was added and the resulting reaction mixture was stirred at −78° C. for 10 min. Next, a solution of I11 (1.0 equiv., 0.387 mmol, 0.149 g) in DMSO (3 ml) was added and the reaction mixture was stirred at −78° C. for 20 min. Triethylamine (4.25 equiv., 1.64 mmol, 0.166 g) was added and stirring was continued for 10 min at −78° C. The reaction mixture was allowed to warm to room temperature and was subsequently quenched with isopropanol (200 μl), after which the resulting mixture was diluted with ethyl acetate (30 ml), washed with a 2% aqueous sodium hypochlorite solution and water. The organic layer was evaporated under reduced pressure and the residue purified by column chromatography (dichloromethane/methanol 99:1) affording 6-(2-methyl-imidazo[1,2-a]-pyridin-6-yl)-pyrido[2',1':2,3]imidazo[4,5-c]isoquinolin-5(6H)-one (75) (2.5 mg, yield=1.8%, purity (LC)=81%).

Example 9

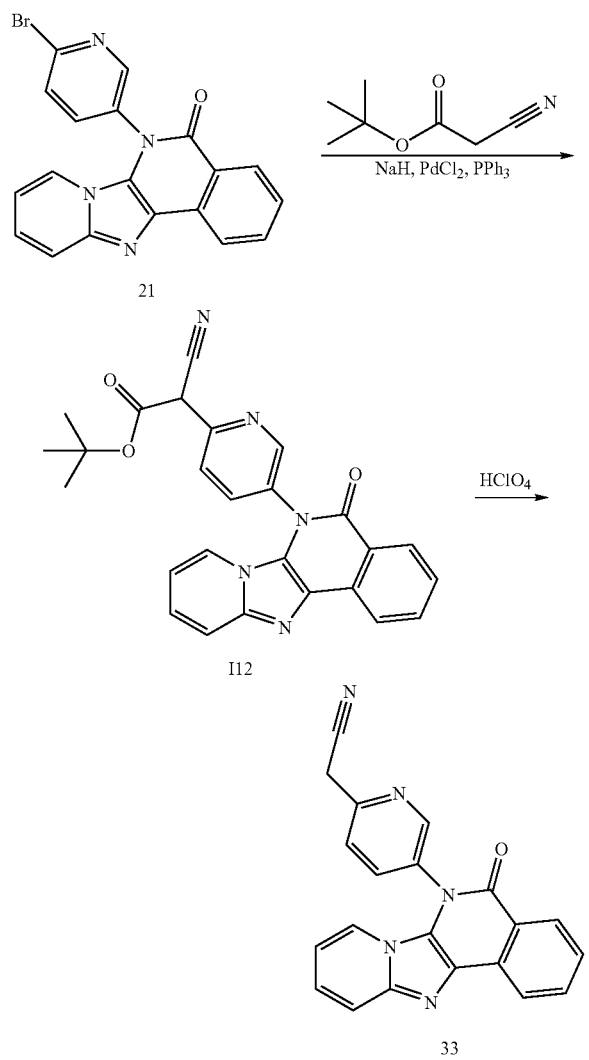

Preparation of the catalyst: Triphenylphosphine (0.3 equiv., 0.115 mmol, 0.030 g) and palladium chloride (0.1 equiv., 0.038 mmol, 0.007 g) were mixed in dry pyridine (1 ml) under Ar atmosphere. The mixture was stirred at 60° C. for 15 min.

Sodium hydride (2.2 equiv., 0.844 mmol, 0.034 g (60%)) was added to a solution of tert-butyl cyanoacetate (1.2 equiv., 0.460 mmol, 0.065 g) in dry pyridine (1 ml) under Ar atmosphere. The catalyst—prepared as described above—was injected, and the mixture was stirred at room temperature for 5 min. Compound 21 (1.0 equiv., 0.383 mmol, 0.150 g) was then added and the reaction mixture was heated at 85° C. for 2 h. After destruction of excess sodium hydride with methanol, the solvent was concentrated under vacuum. The residue was purified by column chromatography (dichloromethane/methanol (7M NH$_3$) 95:5) to give dimethylethyl 5-[5,6-dihydro-5-oxo-pyrido[2',1':2,3]imidazo[4,5-c]isoquinolin-6-yl]-α-cyano-2-pyridineacetate (I12) (0.078 g, yield=45%).

A suspension of I12 (1.0 equiv., 0.172 mmol, 0.078 g) in dry toluene and one drop of perchloric acid was stirred at 85° C. until decarboxylation was finished. The solvent was evaporated, the crude reaction product was brought on a filter and successively washed with isopropanol and isopropylether to give 5-[5,6-dihydro-5-oxo-pyrido[2',1':2,3]-imidazo[4,5-c]isoquinolin-6-yl]-2-pyridineacetonitrile (33) (0.027 g, yield=45%, purity (LC)=90%).

Example 10

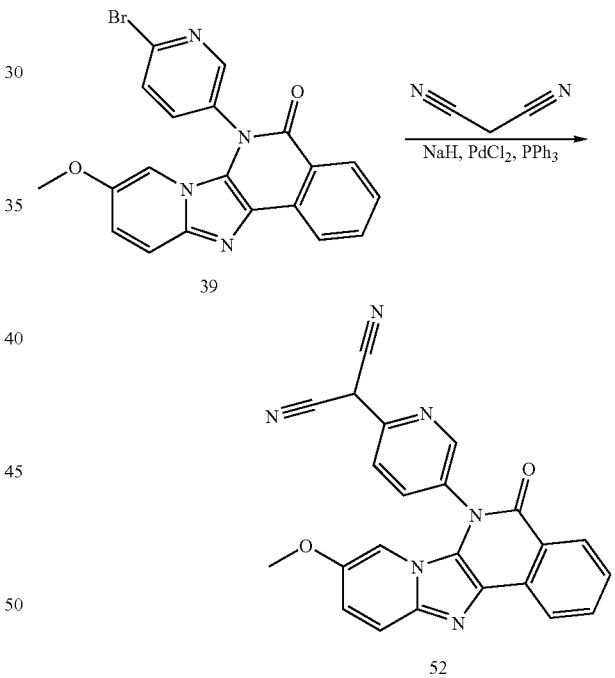

Preparation of the catalyst: Triphenylphosphine (0.3 equiv., 0.114 mmol, 0.030 g) and palladium chloride (0.1 equiv., 0.038 mmol, 0.006 g) were mixed in dry pyridine (1 ml) under Ar atmosphere. The mixture was stirred at 60° C. for 15 min.

Sodium hydride (2.5 equiv., 0.950 mmol, 0.038 g (60%)) was added to a solution of malonitrile (1.2 equiv., 0.456 mmol, 0.030 g) in dry pyridine (1 ml) under Ar atmosphere. The catalyst—prepared as described above—was injected, and the mixture was stirred at room temperature for 5 min. 6-(6-Bromo-pyridin-3-yl)-9-methoxypyrido[2',1':2,3]imidazo[4,5-c]isoquinolin-5(6H)-one (39) (1.0 equiv., 0.380 mmol, 0.160 g) was then added and the reaction mixture was heated at 85° C. for 2 h. After destruction of the excess of sodium hydride with methanol, the solvent was concentrated under vacuum. The residue was purified by column chromatography (gradient elution: dichloromethane/methanol (7M NH₃) 9:1→8:2) to give α-cyano-5-[5,6-dihydro-9-methoxy-5-oxo-pyrido[2',1':2,3]imidazo[4,5-c]isoquinolin-6-yl]-2-pyridineacetonitrile (52) (0.030 g, yield=19%, purity (LC) =99%).

Example 11

1.23-1.33 (4H, m), 1.53-1.60 (2H, m), 2.22 (2H, t, J=7.5 Hz), 5.67 (2H, s), 6.39 (1H, d, J=8.8 Hz), 7.54 (1H, dd, J=8.8, 2.6 Hz), 8.05 (1H, d, J=2.5 Hz), 9.53 (1H, s)

A mixture of compound I14 (1.0 equiv., 6.61 mmol, 1.37 g), 2-chloro-5-isocyanopyridine (1.1 equiv., 7.27 mmol, 1.01 g), methyl 2-formylbenzoate (1.1 equiv., 7.27 mmol, 1.19 g) and perchloric acid (0.2 equiv., 1.43 mmol, 0.14 g) in isopropanol (60 ml) was stirred at room temperature for 5 days. Potassium tert-butoxide (1.2 equiv., 7.93 mmol, 0.89 g) was added and the reaction mixture was further stirred at room temperature for 2 h. Acetic acid (2.00 equiv., 13.22 mmol, 0.79 g) was added, the resulting precipitate was filtered off

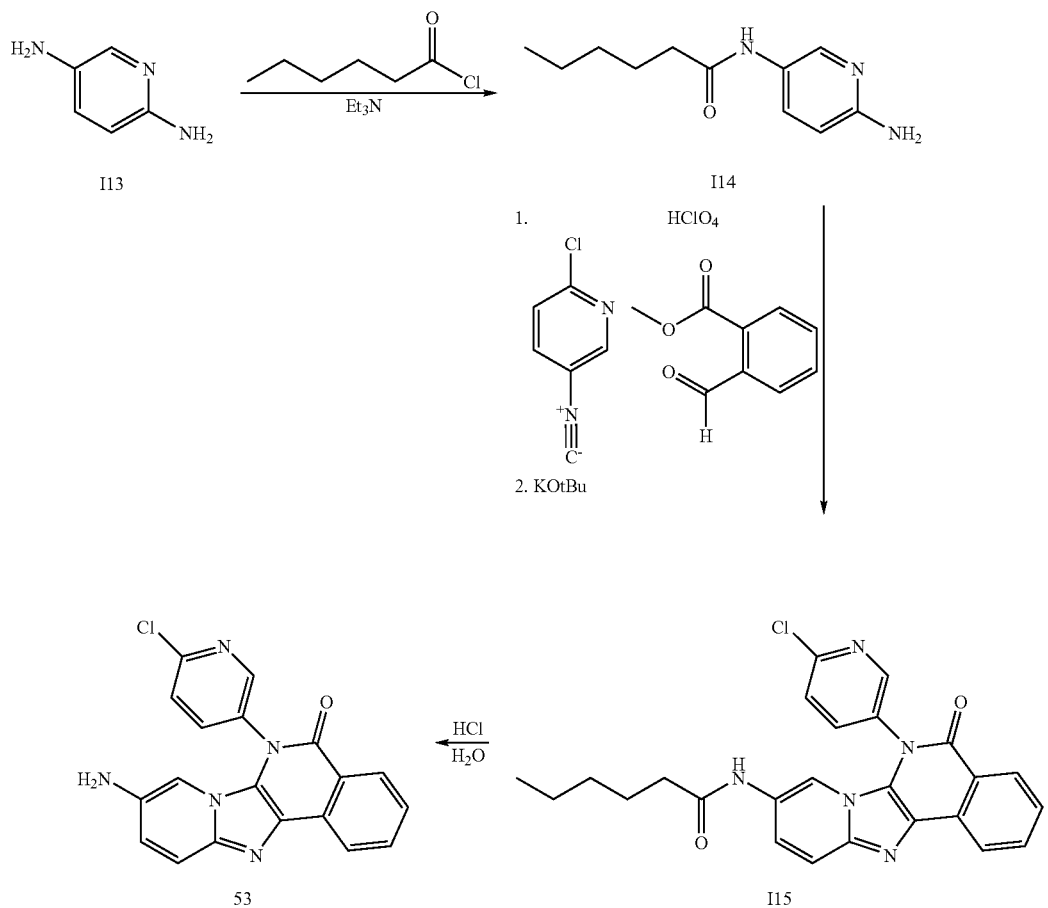

Hexanoyl chloride (1.1 equiv., 10.08 mmol, 1.36 g) was added dropwise to a cooled (0° C.) suspension of 2,5-diaminopyridine (I13) (1.0 equiv., 9.16 mmol, 1.00 g) and triethylamine (1.1 equiv., 10.08 mmol, 1.02 g) in chloroform (100 ml). The reaction mixture was stirred at room temperature for 2 h. The solvent was evaporated under reduced pressure, and the residue was brought on a filter and successively washed with saturated NaHCO₃ solution, water and isopropyl ether. The crude product was further purified by column chromatography (dichloromethane/methanol 95:5; R_f=0.3) to give N-[6-amino-pyridin-3-yl]-hexanamide (I14) (1.24 g, yield=65%). ¹H NMR (6, DMSO-D6): 0.87 (3H, t, J=6.9), and washed with isopropanol and isopropyl ether affording N-[6-(6-chloro-pyridin-3-yl)-5,6-dihydro-5-oxo-pyrido[2',1':2,3]imidazo-[4,5-c]isoquinolin-9-yl]-hexanamide (I15) (1.40 g, yield=46%).

A suspension of compound I15 (1.0 equiv., 0.217 mmol, 0.100 g) in 6 N HCl solution (5 ml) was stirred at 100° C. for 10 h. The solvent was evaporated under reduced pressure. The crude product was brought on a filter and successively washed with saturated NaHCO₃ solution, water, isopropanol and isopropyl ether, and dried in a vacuum oven to give 9-amino-6-(6-chloro-pyridin-3-yl)-pyrido[2',1':2,3]imidazo-[4,5-c]isoquinolin-5(6H)-one (53). (0.046 g, yield=58%, purity (LC)=95%).

Example 12

Scheme B1

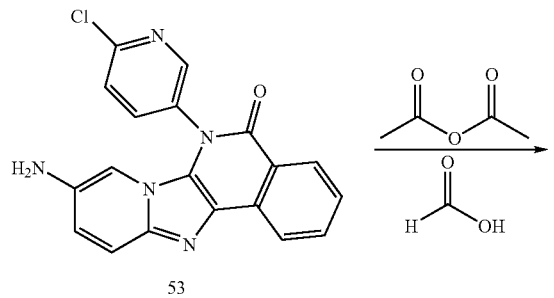

53

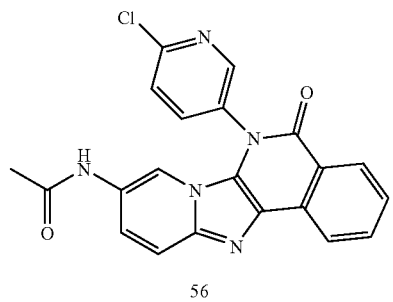

56

Acetic anhydride (1.5 equiv., 0.829 mmol, 0.084 g) was added to a cooled (0° C.) solution of compound 53 (1.0 equiv., 0.553 mmol, 0.200 g) and triethylamine (1.5 equiv., 0.829 mmol, 0.085 g) in dichloromethane (6 ml). The reaction mixture was stirred at room temperature for 20 h. The solvent was evaporated under reduced pressure, and the resulting residue purified by column chromatography (dichloromethane/methanol 9:1; $R_f$=0.3) affording N-[6-(6-chloro-pyridin-3-yl)-5,6-dihydro-5-oxo-pyrido[2',1':2,3]imidazo[4,5-c]isoquinolin-9-yl]-acetamide (56) (0.105 g, yield=47%, purity (LC)=90%).

Example 14

Scheme B3

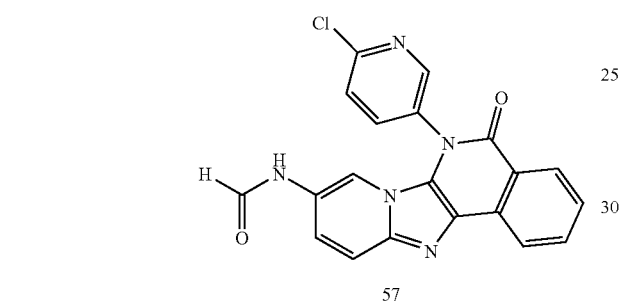

57

Formic acid (5.0 equiv., 1.390 mmol, 0.064 g) was added to a cooled (0° C.) solution of acetic anhydride (2.0 equiv., 0.552 mmol, 0.050 g) in dichloromethane (1 ml). The reaction mixture was stirred at room temperature for 1 h. Compound 53 (1.0 equiv., 0.276 mmol, 0.100 g) was added and the resulting suspension was stirred at room temperature for 6 h. The precipitate was filtered off and successively washed with isopropanol and isopropyl ether affording N-[6-(6-chloro-pyridin-3-yl)-5,6-dihydro-5-oxo-pyrido[2',1':2,3]imidazo[4,5-c]isoquinolin-9-yl]-formamide (57) (0.060 g, yield=56%, purity (LC)=96%).

Example 13

Scheme B2

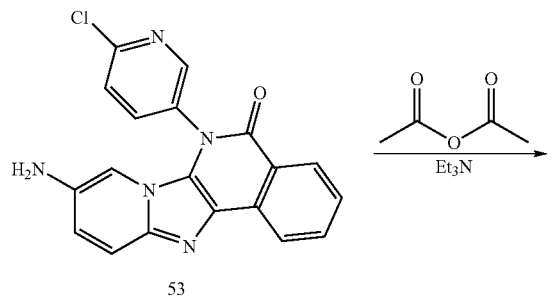

53

61

Trifluoroacetic anhydride (1.2 equiv., 0.664 mmol, 0.139 g) was added dropwise to a cooled (0° C.) solution of compound 53 (1.0 equiv., 0.553 mmol, 0.200 g) and triethylamine (1.5 equiv., 0.830 mmol, 0.084 g) in dichloromethane (6 ml). The reaction mixture was stirred at room temperature for 2 h. The solvent was removed under vacuum. Water was added, the resulting precipitate was filtered off and successively washed with water and isopropyl ether to give N-[6-(6-chloro-pyridin-3-yl)-5,6-dihydro-5-oxo-pyrido[2',1':2,3]

imidazo[4,5-c]isoquinolin-9-yl]-2,2,2-trifluoro-acetamide (61) (0.190 g, yield=75%, purity (LC)=95%).

Example 15

Scheme B4

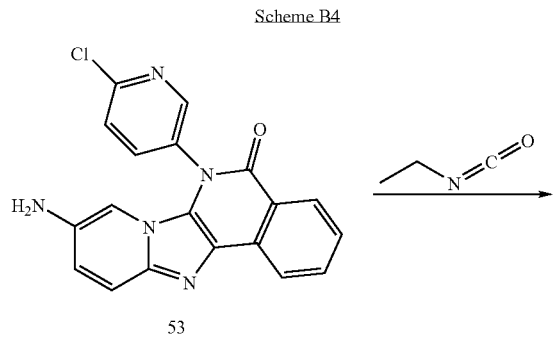

A mixture of compound 53 (1.0 equiv., 0.276 mmol, 0.100 g) and ethyl isocyanate (5.0 equiv., 1.382 mmol, 0.098 g) in chloroform (3 ml) was stirred at room temperature for 9 days. The resulting precipitate was filtered off and successively washed with methanol, isopropanol and isopropyl ether to give 1-ethyl-3-[6-(6-chloro-pyridin-3-yl)-5,6-dihydro-5-oxo-pyrido[2',1':2,3]imidazo[4,5-c]isoquinolin-9-yl]-urea (60) (0.046 g, yield=38%, purity (LC)=90%).

Example 16

Scheme B5

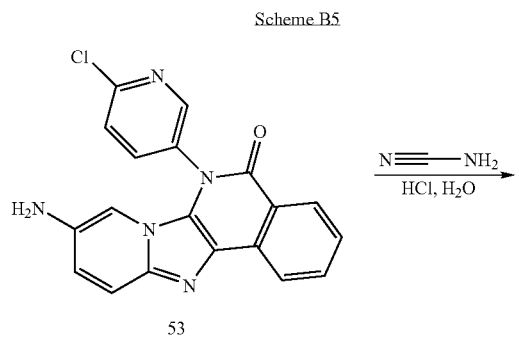

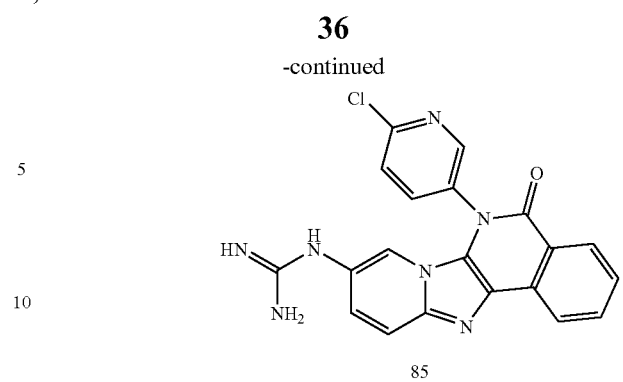

A mixture of compound 53 (1.0 equiv., 0.138 mmol, 0.050 g), cyanamide (20.0 equiv., 2.764 mmol, 0.116 g), a 37% aqueous HCl solution (7.2 equiv., 0.995 mmol, 0.098 g) and water (34.0 equiv., 4.699 mmol, 0.085 g) in ethanol (2.5 ml) was refluxed for 48 h.

The reaction mixture was filtered off, the resulting precipitate was successively washed with a saturated aqueous NaHCO₃ solution, water, isopropanol and isopropyl ether, affording N-[6-(6-chloro-pyridin-3-yl)-5,6-dihydro-5-oxo-pyrido[2',1':2,3]imidazo-[4,5-c]isoquinolin-9-yl]-guanidine (85) (0.008 g, yield=14%, purity (LC)=87%).

Example 17

Scheme B6

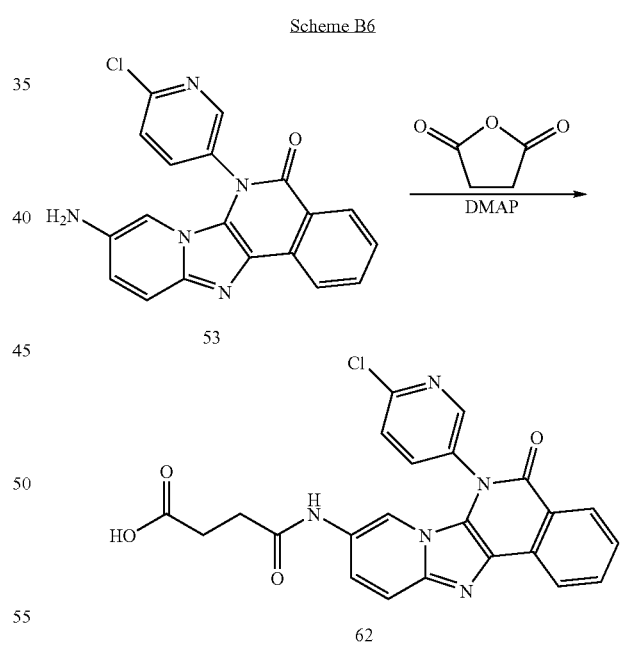

A mixture of compound 53 (1.0 equiv., 0.276 mmol, 0.100 g), succinic anhydride (1.5 equiv., 0.415 mmol, 0.041 g) and 4-dimethylaminopyridine (0.1 equiv., 0.028 mmol, 0.003 g) in DMF (2 ml) was stirred at room temperature for 5 days. Water was added and the resulting precipitate was successively washed with isopropanol and isopropyl ether, affording 4-[[6-(6-chloro-pyridin-3-yl)-5,6-dihydro-5-oxo-pyrido-[2',1':2,3]imidazo[4,5-c]isoquinolin-9-yl]-amino]-4-oxy-butanoic acid (62) (0.042 g, yield=33%, purity (LC)=90%).

Example 18

Scheme B7

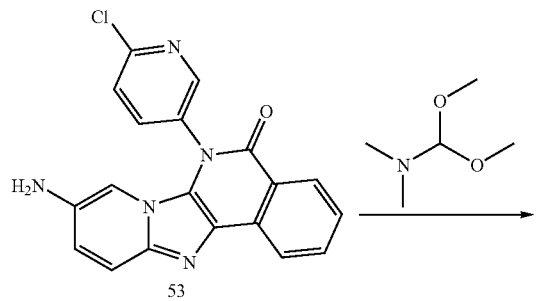

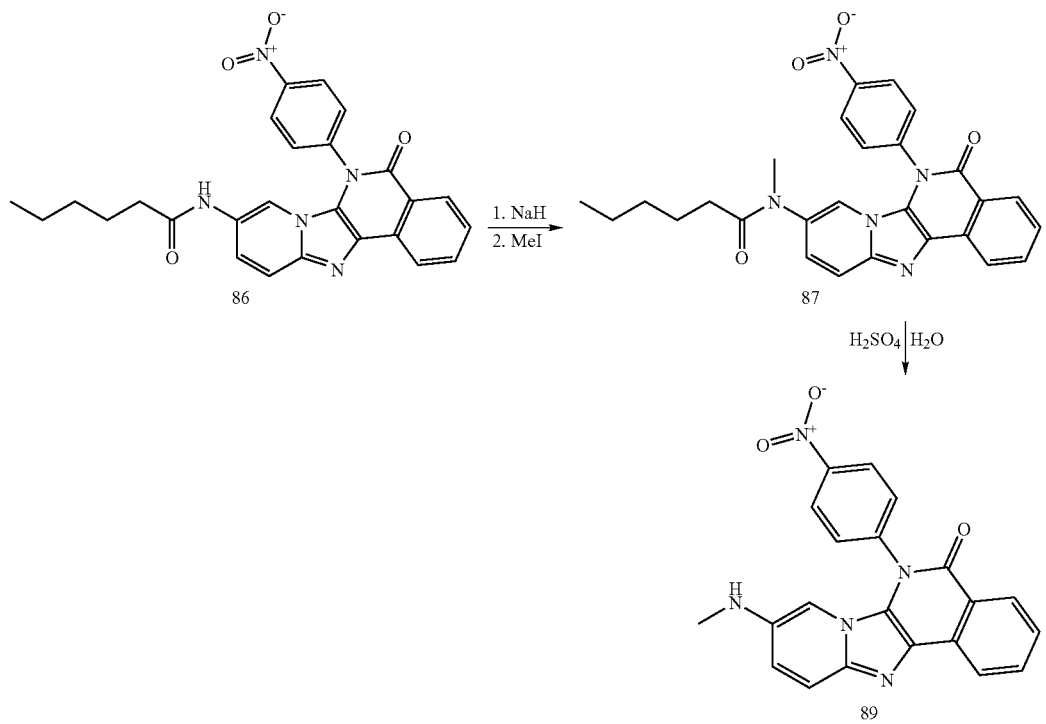

Example 19

Scheme B8

-continued

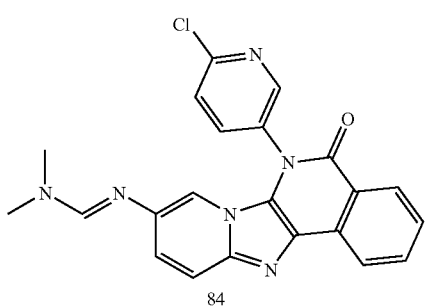

N,N-Dimethylformamide dimethyl acetal (10.0 equiv., 1.935 mmol, 0.231 g) was added to a suspension of compound 53 (1.0 equiv., 0.193 mmol, 0.070 g) in DMF (3 ml). The reaction mixture was stirred overnight at 110° C. The solvent was evaporated under reduced pressure. Isopropyl ether was added and the mixture was brought on a filter and washed with isopropyl ether to give 6-(6-chloro-pyridin-3-yl)-9-[[(dimethylamino)-methylene]amino]-pyrido[2',1':2,3]imidazo[4,5-c]isoquinolin-5(6H)-one (84) (0.050 g, yield=62%, purity (LC)=77%).

N-[5,6-dihydro-6-(4-nitrophenyl)-5-oxo-pyrido[2',1':2,3]imidazo[4,5-c]isoquinolin-9-yl]-hexanamide (86) was synthesized by the same procedure as described for the synthesis of I15 (example 11: scheme B). $^1$H NMR (δ, DMSO-D6): 0.87 (3H, t, J=7.2), 1.13-1.28 (4H, m), 1.37-1.44 (2H, m), 2.15 (2H, t, J=7.1 Hz), 7.04 (1H, d, J=9.7), 7.62-7.67 (2H, m), 7.89 (1H, s), 7.96-7.93 (3H, m), 8.34 (1H, d, J=7.6 Hz), 8.35 (1H, d, J=7.7 Hz), 8.53 (2H, d, J=8.7 Hz), 9.87 (1H, s)

Sodium hydride (1.6 equiv., 1.029 mmol, 0.041 g (60%)) was added to a solution of 86 (1.0 equiv., 0.643 mmol, 0.302 g) in DMF (15 ml), the reaction mixture was stirred for 1 h at room temperature. Methyl iodide (1.2 equiv., 0.772 mmol, 0.110 g) was added and the mixture was stirred at room temperature for 24 h. Water was added to the reaction mixture, and the formed precipitate was filtered off and washed with water and isopropyl ether to give N-[5,6-dihydro-6-(4-nitrophenyl)-5-oxo-pyrido[2',1':2,3]-imidazo[4,5-c]isoquinolin-9-yl]-N-methyl-hexanamide (87) (0.296 g, yield=95%, purity (LC)=93%).

A suspension of 87 (0.612 mmol, 0.296 g) in a 6 M aqueous H$_2$SO$_4$ solution (15 ml) was stirred at 85° C. for 5 h. The mixture was cooled to room temperature, the precipitate was filtered off and successively washed with water, saturated NaHCO$_3$ solution, isopropanol and isopropyl ether to give 9-(methylamino)-6-(4-nitrophenyl)-pyrido[2',1':2,3]imidazo[4,5-c]isoquinolin-5(6H)-one (89) (0.064 g, yield=27%, purity (LC)=97%).

Example 20

2-Amino-5-iodopyridine (I16) (1.0 equiv., 332 mmol, 73.0 g), 2,5-hexanedione (1.2 equiv., 398 mmol, 45.0 g) and p-toluenesulfonic acid (0.1 equiv., 33 mmol, 5.7 g) were dissolved in toluene (300 ml) and heated in a Dean-Stark apparatus for 5 h. After cooling to room temperature, the dark brown reaction mixture was washed with a saturated aqueous NaHCO$_3$ solution, water and brine. The organic phase was dried with MgSO$_4$ and concentrated in vacuo. The resulting dark residue was dried under high vacuum and used in the next step without further purification (89.0 g, yield=90%). $^1$H NMR (δ, CDCl$_3$): 2.13 (6H, s), 5.89 (2H, s), 7.01 (1H, d, J=8.2 Hz), 8.09 (1H, dd, J=8.2, 2.2 Hz), 8.79 (1H, d, J=2.2 Hz)

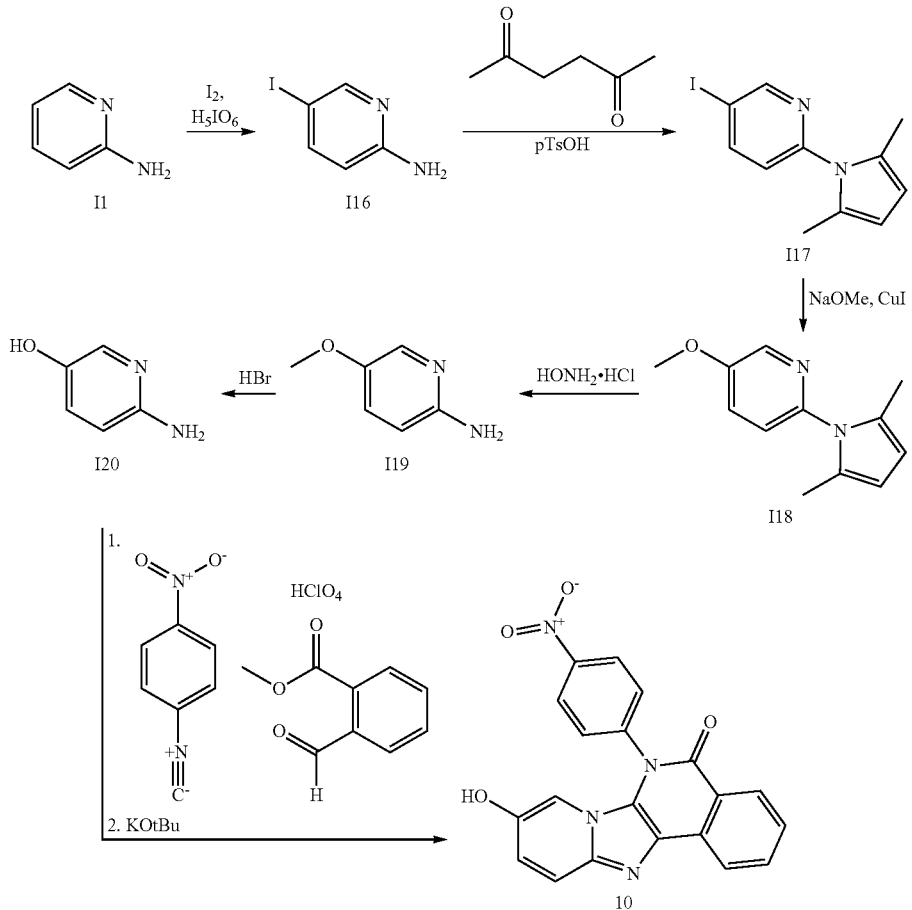

A mixture of 2-aminopyridine (I1) (1.0 equiv., 318 mmol, 30.0 g), periodic acid dihydrate (0.15 equiv., 48 mmol, 10.7 g) and iodine (0.42 equiv., 134 mmol, 32.4 g) was heated in a mixed solution of acetic acid (800 ml), water (36 ml) and sulfuric acid (6.2 ml) at 80° C. for 4 h. The reaction mixture was poured into 10% aqueous Na$_2$S$_2$O$_3$ solution to quench any remaining iodine and extracted with ether. The extract was washed with 10% aqueous NaOH solution, dried (MgSO$_4$) and concentrated in vacuo. The residue was purified by column chromatography (gradient elution: heptane/ethyl acetate 25:75→ethyl acetate) to give 2-amino-5-iodopyridine (I16) (52.0 g, yield=74%). $^1$H NMR (δ, CDCl$_3$): 4.51 (2H, s), 6.35 (1H, d, J=8 Hz), 7.62 (1H, d, J=8 Hz), 8.21 (1H, s)

Sodium (3.0 equiv., 735 mmol, 16.9 g) was dissolved in dry methanol (240 ml). DMF (160 ml), CuI (0.15 equiv., 37 mmol, 7.0 g) and N-protected 2-(2,5-dimethyl-1H-pyrrol-1-yl)-5-iodo-pyridine (I17) (1.0 equiv., 245 mmol, 73.0 g) were added. The reaction mixture was heated to 80° C. for 3 h. After the mixture had been allowed to cool to room temperature, isopropylether and an aqueous NH$_4$Cl solution (5%) were added, the mixture was stirred overnight. The solids were filtered off over Celite and the filtrate was extracted several times with dichloromethane. The combined organic phases were washed with a 10% aqueous NH$_4$OH solution, dried with MgSO$_4$ and concentrated in vacuo. After drying in high vacuum, 2-(2,5-dimethyl-1H-pyrrol-1-yl)-5-methoxy-pyridine (I18) (50 g, yield=100%) was pure enough to be used as such in the next step. $^1$H NMR ($\delta$, CDCl$_3$): 2.08 (6H, s), 3.91 (3H, s), 5.87 (2H, s), 7.15 (1H, d, J=8.7 Hz), 7.32 (1H, dd, J=8.7, 3.0 Hz), 8.27 (1H, d, J=3.0 Hz)

A mixture of I18 (1.0 equiv., 257 mmol, 52.0 g), hydroxylamine hydrochloride (6.5 equiv., 1671 mmol, 69.5 g), triethylamine (2.0 equiv., 514 mmol, 52.0 g), ethanol (400 ml) and water (200 ml) was refluxed for 20 h. The solution was cooled and quenched with 2 M HCl, washed with isopropyl ether and the pH was adjusted to 9-10 with 6 M NaOH. The resulting mixture was extracted several times with dichloromethane. The combined organic phases were dried with MgSO$_4$ and the solvent was removed in vacuo. The oily residue was purified by column chromatography on silica gel (gradient elution: dichloromethane/ethyl acetate 25:75→ethyl acetate) to give 2-amino-5-methoxy-pyridine (I19) (32.0 g, yield=100%). $^1$H NMR ($\delta$, CDCl$_3$): 3.74 (3H, s), 4.45 (2H, s (br)), 6.45 (1H, d, J=8.8 Hz), 7.07 (1H, dd, J=8.8, 3.3 Hz), 7.72 (1H, d, J=3.3 Hz)

A solution of compound I19 in a 48% aqueous HBr solution was refluxed overnight. The reaction mixture was concentrated under reduced pressure. The crude product was purified by column chromatography (dichloromethane/methanol (7M NH$_3$) 9:1) to give 6-amino-pyridin-3-ol (I20) (6.9 g, yield=44%) as dark brown crystals. $^1$H NMR ($\delta$, DMSO-D6): 5.19 (2H, s), 6.33 (1H, d, J=8.7 Hz), 6.90 (1H, dd, J=8.7, 3.0 Hz), 7.50 (1H, d, J=3.0 Hz), 8.61 (1H, s).

A mixture of 2-aminopyridine (I1) (1.0 equiv., 27.2 mmol, 3.00 g), 4-nitrophenyl isocyanide (1.1 equiv., 29.9 mmol, 4.40 g), methyl 2-formylbenzoate (1.1 equiv., 29.9 mmol, 4.9 g) and perchloric acid (0.2 equiv., 5.4 mmol, 0.55 g) in methanol was stirred at room temperature overnight. Potassium tert-butoxide (2.2 equiv., 59.8 mmol, 6.7 g) was added and the reaction mixture was further stirred at room temperature for 2 h. Acetic acid (2.0 ml) (or concentrated hydrochloric acid) was added, the resulting precipitate was filtered off and washed with isopropanol and isopropyl ether to give 9-hydroxy-6-(4-nitrophenyl)-pyrido[2',1':2,3]imidazo[4,5-c]isoquinolin-5(6H)-one (10) (6.80 g, yield=67%, purity (LC)=95%).

Example 21

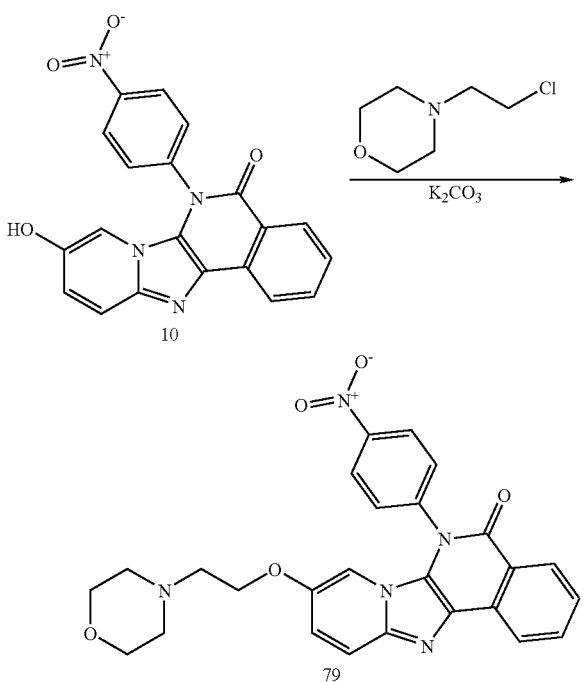

4-(2-Chloroethyl)morpholine hydrochloride (1.2 equiv., 0.806 mmol, 0.121 g) and potassium carbonate (3 equiv., 2.01 mmol, 0.278 g) were added to a solution compound 10 (1.0 equiv., 6.71 mmol, 0.250 g) in DMF (3 ml). The mixture was heated at reflux for 2 h. The reaction product was precipitated by the addition of water, filtered off and washed with isopropanol and isopropyl ether successively to give 9-[2-(4-morpholinyl)-ethoxy]-6-(4-nitrophenyl)-pyrido[2',1':2,3]imidazo[4,5-c]isoquinolin-5(6H)-one (79) (0.156 g, yield=46%, purity (LC)=95%) as a brown powder.

Example 22

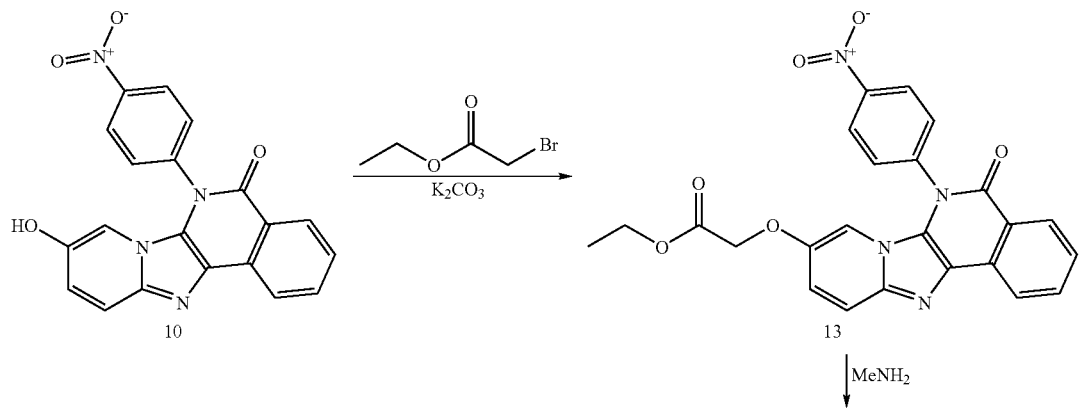

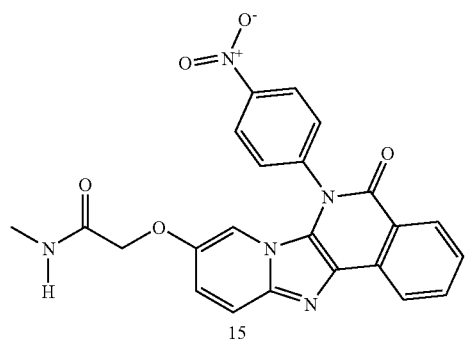

15

Bromoethylacetate (1.2 equiv., 1.128 mmol, 0.188 g) and potassium carbonate (3.0 equiv., 2.820 mmol, 0.390 g) were added to a solution of 10 (1.0 equiv., 0.940 mmol, 0.350 g) in DMF (10 ml). The mixture was heated at reflux for 2 h. The reaction product was precipitated by the addition of water, filtered off and washed with isopropanol and isopropyl ether successively to give ethyl 2-[[5,6-dihydro-6-(4-nitrophenyl)-5-oxo-pyrido[2',1':2,3]imidazo[4,5-c]isoquinolin-9-yl]oxy]-acetate (13) (0.409 g, yield=95%, purity (LC)=92%) as a light red powder.

A mixture of compound 13 (1.0 equiv., 0.22 mmol, 0.100 g) and methylamine (40% in water, 6 ml) in ethanol (8 ml) was heated at 70° C. for 4 h. After cooling, the reaction product was filtered off and washed with isopropanol and isopropylether successively to give N-methyl-2-[[5,6-dihydro-6-(4-nitrophenyl)-5-oxo-pyrido[2',1':2,3]imidazo-[4,5-c]isoquinolin-9-yl]oxy]-acetamide (15) (0.057 g, yield=58%, purity (LC)=98%) as a light yellow powder.

Example 23

Scheme C3

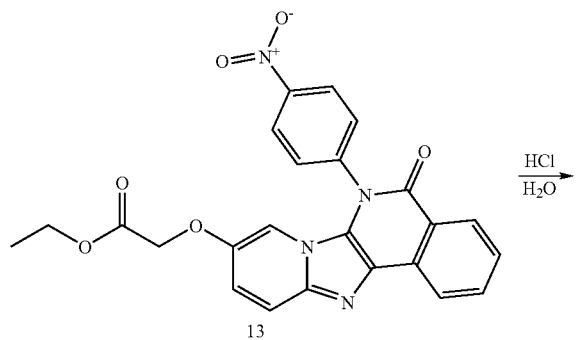

A solution of compound 13 (1.0 equiv., 0.207 g, 0.45 mmol) in a mixture of DMF (5 ml) and concentrated aqueous HCl (10 ml) was heated at reflux for 2 days. After cooling to room temperature, the reaction product was filtered off and washed with isopropanol and isopropylether successively to give the hydrochloride salt of 2-[[5,6-dihydro-6-(4-nitrophenyl)-5-oxo-pyrido[2',1':2,3]imidazo[4,5-c]isoquinolin-9-yl]oxy]-acetic acid (14) (0.165 g, yield=96%, purity (LC)=90%) as a light brown powder.

Example 24

Scheme C4

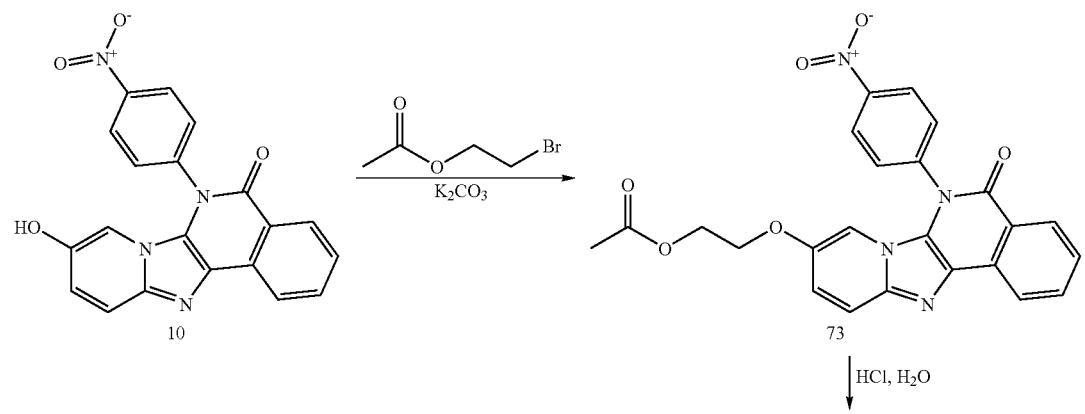

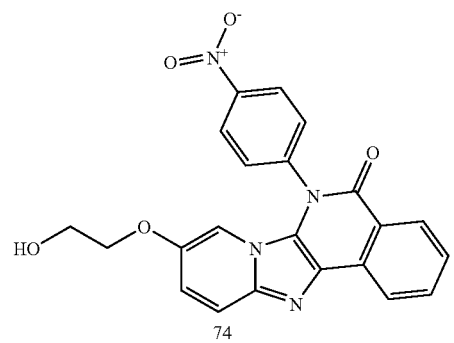

A mixture of compound 10 (1.0 equiv., 0.806 mmol, 0.300 g), 2-bromoethyl acetate (2.0 equiv., 1.611 mmol, 0.269 g) and K$_2$CO$_3$ (3.0 equiv., 2.417 mmol, 0.334 g) in dry DMF (5 ml) was stirred at 60° C. for 4 h. Water was added to the reaction mixture and the aqueous layer was extracted with dichloromethane. The combined organic layers were dried with MgSO$_4$ and concentrated in vacuo. Purification by column chromatography (dichloromethane/methanol 97.2:2.5) afforded 6-(4-nitrophenyl)-9-[2-[(1-oxoethyl)oxy]-ethoxy]-pyrido[2',1':2,3]imidazo[4,5-c]isoquinolin-5(6H)-one (73) (0.245 g, yield=66%, purity (LC)=97%).

A solution of compound 73 (0.327 mmol, 0.150 g) in concentrated aqueous HCl was stirred at room temperature overnight. The solvent was evaporated under vacuum and the crude reaction product was brought on a filter and washed with isopropanol and isopropylether successively to give the hydrochloride salt of 9-[2-hydroxy-ethoxy]-6-(4-nitrophenyl)-pyrido[2',1':2,3]imidazo[4,5-c]isoquinolin-5(6H)-one (74) (0.148 g, yield=100%, purity (LC)=95%).

Example 25

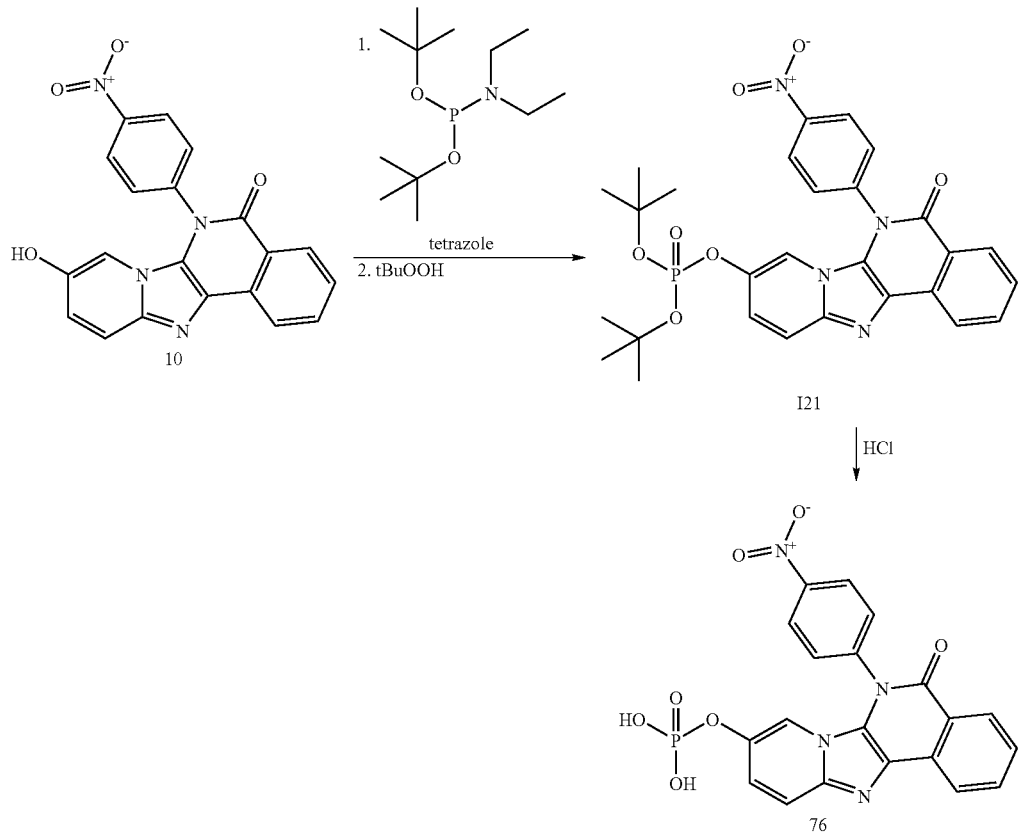

Tetrazole (2.0 equiv., 5.37 mmol, 0.38 g) and di-(tert-butyl) diethylphosphoramidite (1.6 equiv., 4.30 mmol, 1.07 g) were added to a solution of 10 (1.0 equiv., 2.69 mmol, 1.00 g) in anhydrous acetonitrile under Ar atmosphere. The reaction mixture was stirred at room temperature for 1 h. A 70% tert-butyl hydroperoxide solution in water (5.0 equiv., 13.45 mmol, 1.73 g) was added slowly and stirring was continued for 1 h. The reaction mixture was filtered through a glass filter and the filtrate was evaporated under reduced pressure. Purification by column chromatography (dichloromethane/methanol 97.2:2.5) afforded phosphoric acid di-tert-butyl ester 6-(4-nitrophenyl)-5-oxo-5,6-dihydro-pyrido[2',1':2,3] imidazo[4,5-c]isoquinolin-9-yl ester (I21). A suspension of I21 in a 4 M HCl solution in isopropanol was stirred at room temperature overnight. The solvent was removed under reduced pressure to give phosphoric acid 5,6-dihydro-6-(4-nitrophenyl)-5-oxo-pyrido[2',1':2,3]imidazo[4,5-c]iso-quinolin-9-yl ester (76) as a hydrochloride salt (0.47 g, yield=36%, purity (LC)>95%).

Example 26

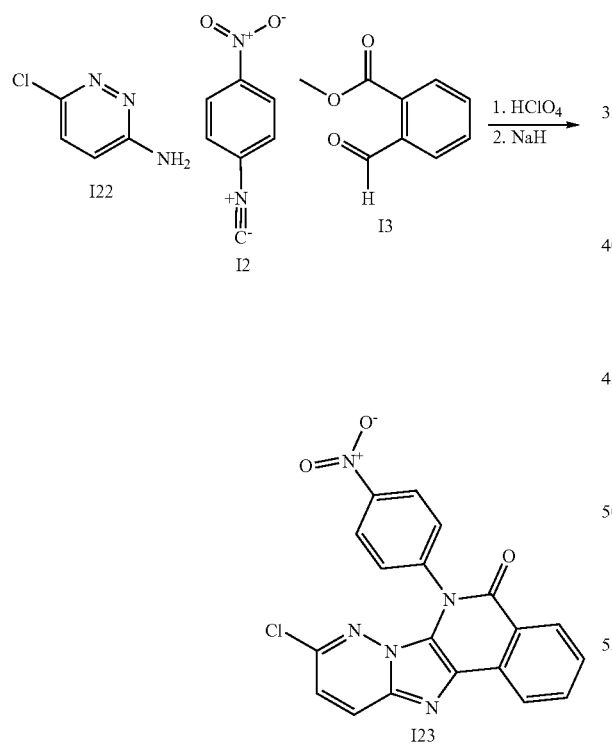

A mixture of 6-chloropyridazin-3-amine (I122) (1.0 equiv., 7.72 mmol, 1.00 g), 4-nitrophenyl isocyanide (I2) (1.2 equiv., 9.26 mmol, 1.37 g) and methyl 2-formylbenzoate (I3) (1.2 equiv., 9.26 mmol, 1.52 g) and perchloric acid (0.1 equiv., 0.77 mmol, 0.078 g) in THF (40 ml) was heated at 50° C. overnight under Ar atmosphere. After the reaction mixture had been cooled in an ice-bath, sodium hydride (1.5 equiv., 11.58 mmol, 0.463 g (60%)) was added. The reaction mixture was stirred at room temperature overnight and then poured onto a mixture of acetonitrile (30 ml) and 1 M HCl (30 ml). The resulting precipitate was filtered off, washed with isopropanol and isopropyl ether successively to give 9-chloro-6-(4-nitrophenyl)-pyridazo[3',2':2,3]-imidazo[4,5-c]isoquinolin-5(6H)-one (I23) (0.554 g, yield=18%) as a light green powder.

Example 27

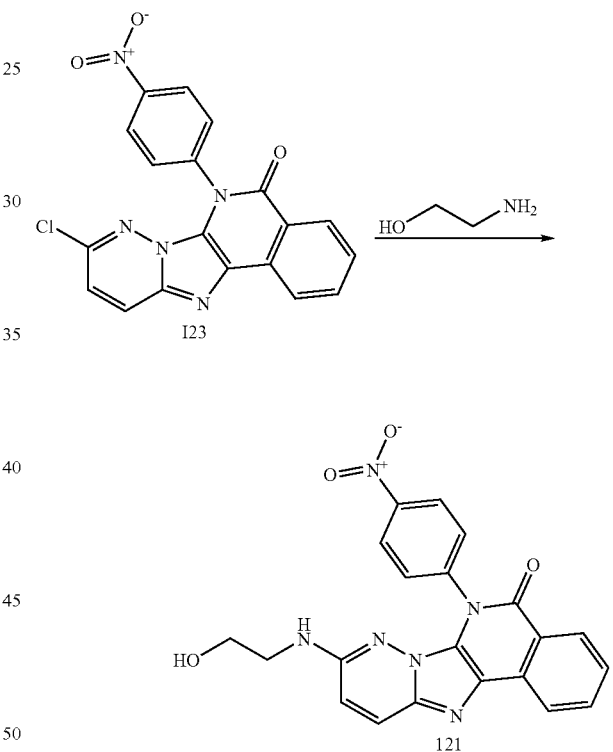

A mixture of I23 (1.0 equiv., 1.28 mmol, 0.500 g) and ethanolamine (3.0 equiv., 3.84 mmol, 0.234 g) in DMSO (20 ml) was heated at 160° C. for 2 h. The reaction product was precipitated by the addition of water, filtered off and successively washed with isopropanol and isopropyl ether. Purification by flash chromatography (gradient elution: dichloromethane/methanol 98:2→95/5) gave 9-[(2-hydroxyethyl)amino]-6-(4-nitrophenyl)-pyridazo[3',2':2,3]imidazo[4,5-c]isoquinolin-5(6H)-one (121) (0.257 g, yield=46%, purity (LC)=94%) as an orange powder.

Example 28

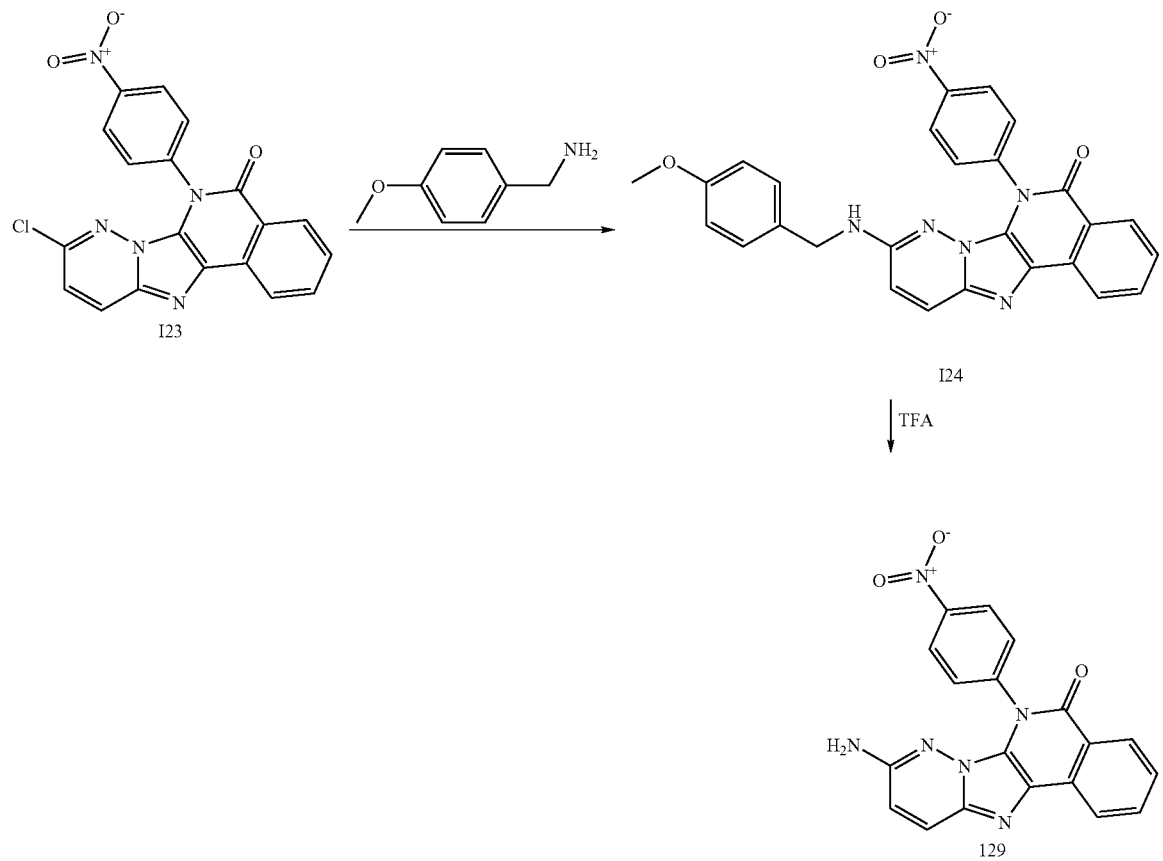

4-Methoxybenzylamine (5.0 equiv., 1 mmol, 0.140 g) was added to a solution of compound I23 (1.0 equiv., 0.20 mmol, 0.100 g) in DMSO (5 ml) and the mixture was heated to 150° C. for 5 h. The compound was precipitated from the reaction mixture by the addition of water. The precipitate was isolated by filtration and successively washed with isopropanol and isopropyl ether to afford 9-[[(4-methoxyphenyl)methyl]amino]-6-(4-nitrophenyl)-pyridazo[3',2':2,3]imidazo[4,5-c]isoquinolin-5(6H)-one (I24) (0.082 g, yield=68%, purity (LC)>95%) as an orange powder.

Compound I24 (1.0 equiv., 0.14 mmol, 0.082 g) was mixed with trifluoroacetic acid (3 ml) and heated at 65° C. for 1 h. The solvents were evaporated under reduced pressure. The residue was dissolved in ethyl acetate and washed with a 2 N aqueous NaOH solution. During neutralization, the reaction product precipitated from the ethyl acetate solution. The product was isolated by filtration and washed with isopropanol and isopropyl ether successively to afford 9-amino-6-(4-nitrophenyl)-pyridazo-[3',2':2,3]imidazo[4,5-c]isoquinolin-5(6H)-one (I29) (0.051 g, yield=99%, purity (LC)=98%) as an orange powder.

Example 29

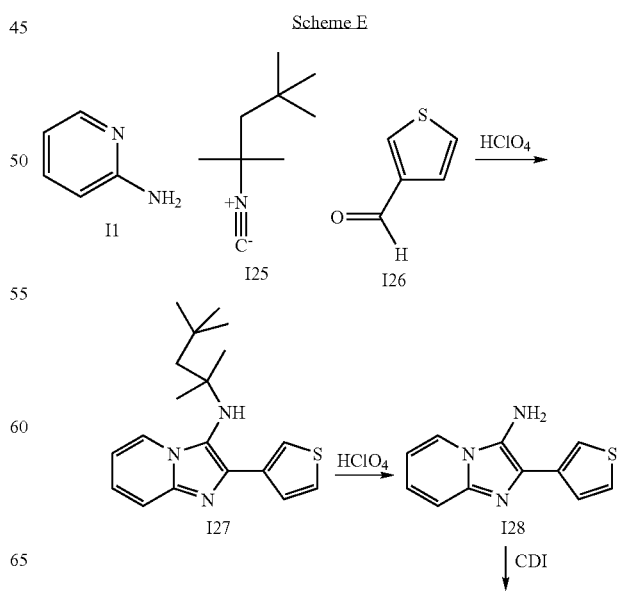

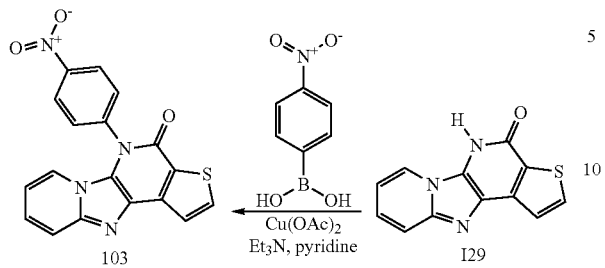

A mixture of 2-aminopyridine (I1) (1.0 equiv., 5.31 mmol, 0.500 g), 1,1,3,3-tertramethylbutyl-isonitrile (I25) (1.2 equiv., 6.38 mmol, 0.888 g) and 3-thiophene-carboxaldehyde (I26) (1.2 equiv., 6.38 mmol, 0.715 g) and a catalytic amount of perchloric acid (1 drop) in methanol (3 ml), was stirred overnight at room temperature under Ar atmosphere. The solvent was evaporated under reduced pressure and the residue was taken up in dichloromethane. An excess of perchloric acid (1 ml) was added and the reaction mixture was heated at 50° C. for 3 h. The resulting precipitate was filtered off, successively washed with isopropanol and isopropyl ether to give 2-(thiophen-3-yl)-imidazo[1,2-a]pyridin-3-amine (I28) (1.134 g, yield=99%) as a light brown powder.

A mixture of I28 (2.32 mmol, 0.500 g) and carbonyldiimidazole (1.5 equiv., 3.48 mmol, 0.565 g) in 1,2-dichlorobenzene (10 ml) was heated at 180° C. for 4 h under Ar atmosphere. The mixture was allowed to cool to room temperature, the precipitate was filtered off and washed with acetone to afford product pyrido[2',1':2,3]imidazo-[4,5-b]thieno[3,2-d]pyridin-4(5H)-one (I29) (0.310 g, yield=55%) as a grey powder.

A mixture of compound I29 (1.0 equiv., 0.32 mmol, 0.077 g), 4-nitrophenylboronic acid (2.0 equiv., 0.64 mmol, 0.110 g), copper(II) acetate (1.5 equiv., 0.48 mmol, 0.087 g), pyridine (2.0 equiv., 0.64 mmol, 0.050 g), triethylamine (2.0 equiv., 0.64 mmol, 0.065 g) and an excess of molecular sieves (powder, 4A) in dichloromethane (3 ml), was stirred at room temperature overnight. The reaction mixture was diluted with dichloromethane and filtered over decalite. The filtrate was washed with an aqueous saturated NaHCO₃ solution and dried with MgSO₄. The solvent was evaporated under reduced pressure, the residue was purified by flash chromatography on silica gel (gradient elution: dichloromethane/ ethyl acetate 95:5→90:10) to afford product 5-(4-nitrophenyl)-pyrido[2',1':2,3]imidazo[4,5-b]thieno[3,2-d]pyridin-4(5H)-one (103) (0.010 g, yield=9%, purity (LC)=95%).

Example 30

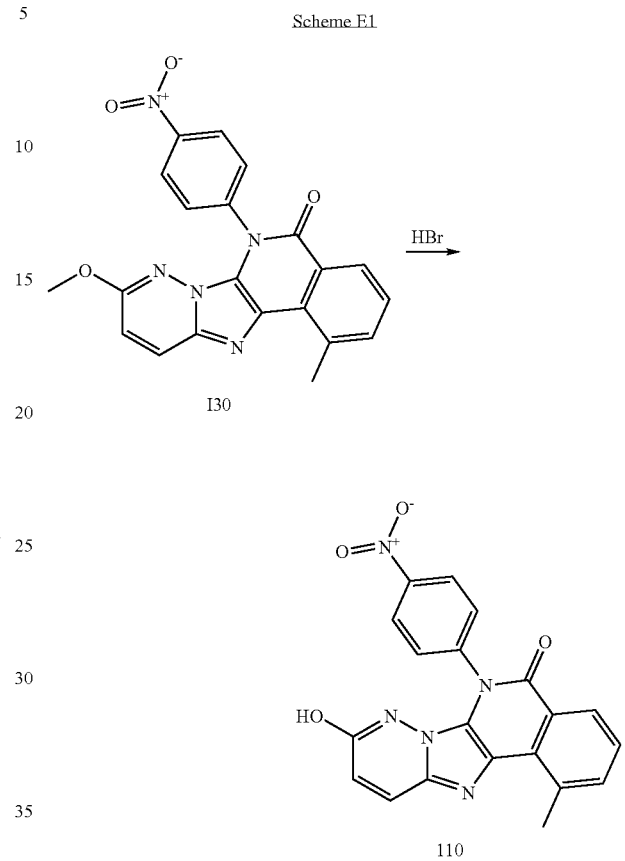

A suspension of 9-methoxy-1-methyl-6-(4-nitrophenyl)-pyrido[2',1':2,3]imidazo-[4,5-c]isoquinolin-5(6H)-one (I30) (0.14 mmol, 0.056 g) in a concentrated aqueous HBr solution (5 ml) was refluxed overnight. The reaction mixture was concentrated under reduced pressure. The crude product was brought on a filter and washed with isopropanol and isopropylether to give the hydrobromide salt of 9-hydroxy-1-methyl-6-(4-nitrophenyl)-pyrido[2',1':2,3]imidazo[4,5-c]isoquinolin-5(6H)-one (110) (0.010 g, yield=17%, purity (LC) =91%).

Example 31

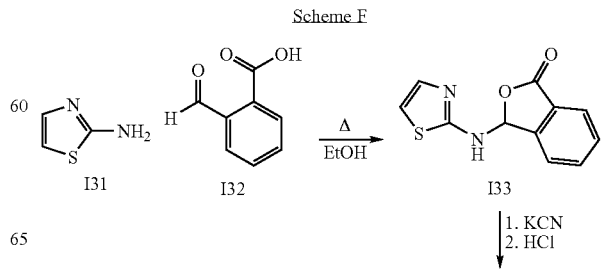

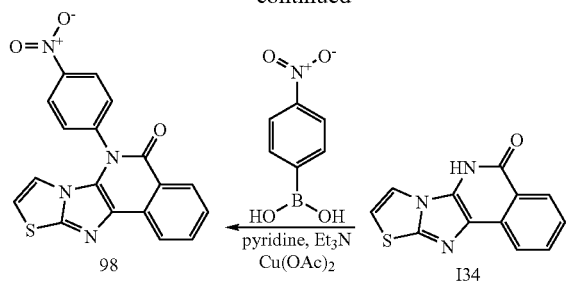

2-Aminothiazole (I31) (1.0 equiv., 5.00 mmol, 0.500 g) and 2-formylbenzoic acid (I32) (1.2 equiv., 6.00 mmol, 0.900 g) were mixed in ethanol (8 ml) and heated at reflux for 2 h. Upon cooling, a precipitate was formed. The product was isolated by filtration and washed with isopropyl ether to afford 3-(2-thiazolylamino)-isobenzofuran-1(3H)-one (I33) (0.944 g, yield=81%).

KCN (1.1 equiv., 1.89 mmol, 0.123 g) was added to a stirred suspension of compound 133 (1.0 equiv., 1.72 mmol, 0.400 g) in ethanol (4 ml), and the reaction mixture was heated at reflux for 1.5 h. The mixture was allowed to cool to room temperature and was subsequently treated with aqueous concentrated HCl (1 ml). The resulting suspension was stirred for 1 h and filtered. The precipitate was washed with ethanol and isopropyl ether to afford thiazolo[2',3':2,3]imidazo[4,5-c]isoquinolin-5(6H)-one (I34) (0.143 g, yield=34%).

4-Nitrophenylboronic acid (2.0 equiv., 0.83 mmol, 0.138 g), pyridine (2.0 equiv., 0.83 mmol, 0.066 g), triethylamine (2.0 equiv., 0.83 mmol, 0.084 g), copper(II) acetate (1.5 equiv., 0.62 mmol, 0.113 g) were added to a stirred solution of compound I34 (1.0 equiv., 0.41 mmol, 0.100 g) in dichloromethane (5 ml). After the addition of excess powdered molecular sieves (4 Å), the reaction mixture was stirred for 3 days in a closed reaction vessel at room temperature. The mixture was diluted by the addition of extra dichloromethane (25 ml), stirred for 1 h and filtered over a short path of decalite. The filtrate was washed with a saturated aqueous solution of NaHCO$_3$, dried with MgSO$_4$ and concentrated under reduced pressure to a final volume of 2 ml. Ethanol (10 ml) was added and the mixture was stirred overnight in an open recipient, allowing the reaction product to crystallize from the solution. Filtration afforded 6-(4-nitrophenyl)-thiazolo[2',3':2,3]imidazo[4,5-c]isoquinolin-5(6H)-one (98) (0.032 g, yield=21%, purity (LC)=93%).

The following tables list examples of compounds of the present invention prepared using similar preparation methods to those of the foregoing synthesis examples. The column 'synthesis scheme' in this table refers to the synthesis scheme illustrated in the above examples, for example synthesis scheme A is illustrated in example 1. The dotted lines indicate the chemical bonds linking the respective groups to the remainder of the molecule.

TABLE 1

| Comp N° | R$^{1a}$ | R$^{1b}$ | R$^3$ | Synthesis Scheme | Salt Form |
|---|---|---|---|---|---|
| 1 | H | H | O$_2$N—C$_6$H$_4$— | A | |
| 2 | N≡C— | H | O$_2$N—C$_6$H$_4$— | A | |
| 3 | H$_3$C— | H | O$_2$N—C$_6$H$_4$— | A | |

TABLE 1-continued
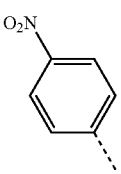
| Comp Nº | R¹ᵃ | R¹ᵇ | R³ | Synthesis Scheme | Salt Form |
|---|---|---|---|---|---|
| 4 | Cl- | H | 4-O₂N-C₆H₄- | A | |
| 5 | I- | H | 4-O₂N-C₆H₄- | A | |
| 6 | -CH₂OH | H | 4-O₂N-C₆H₄- | A1 | |
| 7 | F- | H | 4-O₂N-C₆H₄- | A | |
| 8 | CH₃O- | H | 4-O₂N-C₆H₄- | A | |
| 9 | H | -CH₂OH | 4-O₂N-C₆H₄- | A1 | |
| 10 | HO- | H | 4-O₂N-C₆H₄- | C | |

TABLE 1-continued

| Comp N° | R¹ᵃ | R¹ᵇ | R³ | Synthesis Scheme | Salt Form |
|---|---|---|---|---|---|
| 11 | methyl ester (–OC(O)CH₃ type: methoxycarbonyl) | H | 4-O₂N-C₆H₄– | A1 | |
| 12 | H | H₃C– | 4-O₂N-C₆H₄– | A | |
| 13 | EtO-C(O)-CH₂-O– | H | 4-O₂N-C₆H₄– | C2 | |
| 14 | HO-C(O)-CH₂-O– | H | 4-O₂N-C₆H₄– | C3 | chlorohydrate |
| 15 | CH₃NH-C(O)-CH₂-O– | H | 4-O₂N-C₆H₄– | C2 | |
| 16 | (CH₃)₂N-C(O)-CH₂-O– | H | 4-O₂N-C₆H₄– | C2 | |
| 17 | H₂N-C(O)-CH₂-O– | H | 4-O₂N-C₆H₄– | C2 | |
| 18 | H | H | 2-Cl-pyridin-5-yl | A | |

TABLE 1-continued

| Comp N° | R^(1a) | R^(1b) | R^3 | Synthesis Scheme | Salt Form |
|---|---|---|---|---|---|
| 19 | H | H | 6-methylpyridin-3-yl | A | |
| 20 | H | H | pyridin-3-yl | A | |
| 21 | H | H | 6-bromopyridin-3-yl | A | |
| 22 | H | H | 4-methyl-3-nitrophenyl | F | |
| 23 | H | H | 6-methoxypyridin-3-yl | A | |
| 24 | H | H | 4-(methoxycarbonyl)phenyl | A | |
| 25 | H | H | 4-carboxyphenyl | A2 | chlorohydrate |

TABLE 1-continued
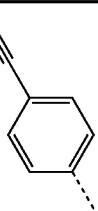
| Comp N° | R$^{1a}$ | R$^{1b}$ | R$^3$ | Synthesis Scheme | Salt Form |
|---|---|---|---|---|---|
| 26 | H | H | 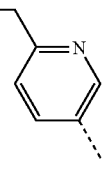 | A | |
| 27 | H | H | 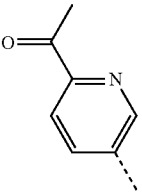 | A6 | |
| 28 | H | H | 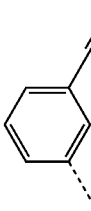 | A6 | |
| 29 | H | H | 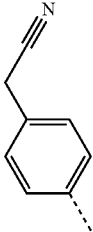 | A | |
| 30 | H | H | 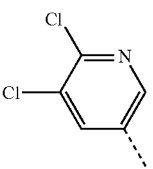 | A | |
| 31 | H | H | 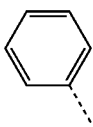 | A | |
| 32 | H | H |  | A | |

TABLE 1-continued
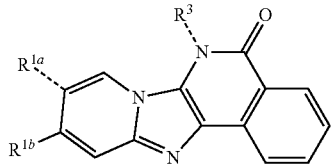
| Comp N° | R^{1a} | R^{1b} | R^3 | Synthesis Scheme | Salt Form |
|---|---|---|---|---|---|
| 33 | H | H | 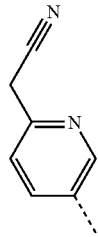 | A8 | |
| 34 | H | H | 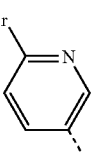 | A | |
| 35 | HO--- | H | 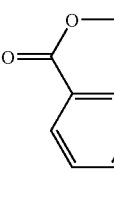 | C | |
| 36 | HO--- | H | 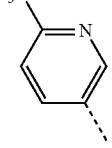 | C | |
| 37 | HO--- | H | 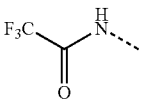 | C | |
| 38 | 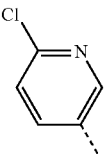 | H | 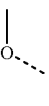 | B3 | |
| 39 | 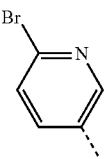 | H | (Br-pyridyl) | A | |

TABLE 1-continued

| Comp N° | R¹ᵃ | R¹ᵇ | R³ | Synthesis Scheme | Salt Form |
|---|---|---|---|---|---|
| 40 | CH₃O- | H | 4-acetylphenyl | F | |
| 41 | HO- | H | 6-chloropyridin-3-yl | C | |
| 42 | HO- | H | 4-cyanophenyl | C | Chlorohydrate |
| 43 | HO- | H | 6-methylpyridin-3-yl | C | Chlorohydrate |
| 44 | HO- | H | 6-bromopyridin-3-yl | C | Chlorohydrate |
| 45 | CH₃O- | H | (5-methylpyridin-2-yl)methyl | A6 | |
| 46 | HO- | H | (5-methylpyridin-2-yl)methyl | A6 | |

TABLE 1-continued
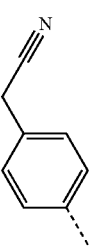
| Comp N° | R1a | R1b | R3 | Synthesis Scheme | Salt Form |
|---|---|---|---|---|---|
| 47 | HO- | H | 4-(cyanomethyl)phenyl | C | Chlorohydrate |
| 48 | H | H3C-O- | 2-chloropyridin-5-yl | A | |
| 49 | HO- | H3C-O- | 4-nitrophenyl | C | Chlorohydrate |
| 50 | HO- | H3C-O- | 2-chloropyridin-5-yl | C | Chlorohydrate |
| 51 | HO- | H | phenyl | C | Chlorohydrate |
| 52 | CH3-O- | H | 2-(dicyanomethyl)pyridin-5-yl | A9 | |
| 53 | H2N- | H | 2-chloropyridin-5-yl | B | |

TABLE 1-continued

| Comp Nº | R¹ᵃ | R¹ᵇ | R³ | Synthesis Scheme | Salt Form |
|---|---|---|---|---|---|
| 54 | methoxy | H | 2-chloropyridin-5-yl | A | |
| 55 | hydroxymethyl | H | 2-chloropyridin-5-yl | A1 | |
| 56 | acetamido | H | 2-chloropyridin-5-yl | B2 | |
| 57 | formamido | H | 2-chloropyridin-5-yl | B1 | |
| 58 | F | H | 2-chloropyridin-5-yl | A | |
| 59 | Cl | H | 2-chloropyridin-5-yl | A | |
| 60 | 3-ethylureido | H | 2-chloropyridin-5-yl | B4 | |
| 61 | trifluoroacetamido | H | 2-chloropyridin-5-yl | B3 | |

TABLE 1-continued

| Comp N° | R$^{1a}$ | R$^{1b}$ | R$^3$ | Synthesis Scheme | Salt Form |
|---|---|---|---|---|---|
| 62 | HOOC-CH$_2$-CH$_2$-C(O)-NH- | H | 2-chloro-pyridin-5-yl | B6 | |
| 63 | HO- | H | 3-fluoro-4-methyl-phenyl | C | Chlorohydrate |
| 64 | (CH$_3$)$_2$N-CH$_2$CH$_2$CH$_2$-N(CH$_3$)- | H | 4-nitrophenyl | A4 | |
| 65 | 4-methylpiperazin-1-yl | H | 4-nitrophenyl | A4 | |
| 66 | morpholin-4-yl-CH$_2$CH$_2$-NH- | H | 4-nitrophenyl | A4 | |
| 67 | pyrrolidin-1-yl-CH$_2$CH$_2$-NH- | H | 4-nitrophenyl | A4 | |
| 68 | (CH$_3$)$_2$N-CH$_2$CH$_2$-N(CH$_3$)- | H | 4-nitrophenyl | A4 | |

TABLE 1-continued

| Comp N° | R¹ᵃ | R¹ᵇ | R³ | Synthesis Scheme | Salt Form |
|---|---|---|---|---|---|
| 69 | CH₃C(O)NH- | H | 4-O₂N-C₆H₄- | A4 | |
| 70 | HC(O)NH- | H | 4-O₂N-C₆H₄- | A4 | |
| 71 | HOOC- | H | 4-O₂N-C₆H₄- | A2 | |
| 72 | H₂NC(O)- | H | 4-O₂N-C₆H₄- | A | |
| 73 | CH₃C(O)OCH₂CH₂O- | H | 4-O₂N-C₆H₄- | C4 | |
| 74 | HOCH₂CH₂O- | H | 4-O₂N-C₆H₄- | C4 | Chlorohydrate |
| 75 | H | H | 2-methyl-imidazo[1,2-a]pyridin-6-yl | A7 | |

TABLE 1-continued

| Comp N° | R¹ᵃ | R¹ᵇ | R³ | Synthesis Scheme | Salt Form |
|---|---|---|---|---|---|
| 76 | phosphate (HO)(HO)P(=O)O— | H | 4-O₂N-C₆H₄— | C5 | Chlorohydrate |
| 77 | phosphate (HO)(HO)P(=O)O— | H | 2-chloro-pyridin-5-yl | C5 | Chlorohydrate |
| 78 | pyrrolidin-1-yl-ethoxy | H | 4-O₂N-C₆H₄— | C1 | |
| 79 | morpholin-4-yl-ethoxy | H | 4-O₂N-C₆H₄— | C1 | |
| 80 | piperidin-1-yl-ethoxy | H | 4-O₂N-C₆H₄— | C1 | |
| 81 | (CH₃)₂N-CH₂CH₂-O— | H | 4-O₂N-C₆H₄— | C1 | |
| 82 | (CH₃)₂N-CH₂CH₂CH₂-O— | H | 4-O₂N-C₆H₄— | C1 | |
| 83 | (CH₃)₂N-CH₂CH₂CH₂-O— | H | 2-chloro-pyridin-5-yl | C1 | |

TABLE 1-continued

| Comp Nº | R¹ᵃ | R¹ᵇ | R³ | Synthesis Scheme | Salt Form |
|---|---|---|---|---|---|
| 84 | (CH₃)₂N-CH=N- | H | 2-chloro-pyridin-5-yl | B7 | |
| 85 | HN=C(NH₂)-NH- | H | 2-chloro-pyridin-5-yl | B5 | |
| 86 | CH₃(CH₂)₄C(O)NH- | H | 4-O₂N-C₆H₄- | B | |
| 87 | CH₃(CH₂)₄C(O)N(CH₃)- | H | 4-O₂N-C₆H₄- | B8 | |
| 88 | H₂N- | H | 4-O₂N-C₆H₄- | B | |
| 89 | CH₃NH- | H | 4-O₂N-C₆H₄- | B8 | |
| 90 | F₃C-C(O)-NH- | H | 4-O₂N-C₆H₄- | B3 | |

TABLE 2

| Comp N° | R¹ᶜ | R³ | Synthesis Scheme | Salt Form |
|---|---|---|---|---|
| 91 | CH₃ | 4-O₂N-C₆H₄ | A | |
| 92 | methyl ester (−C(O)OCH₃) | 2-Cl-pyridin-5-yl | A1 | |
| 93 | Br | 2-Cl-pyridin-5-yl | A | |
| 94 | methyl ester (−C(O)OCH₃) | 4-O₂N-C₆H₄ | A1 | |
| 95 | carboxylic acid (−C(O)OH) | 4-O₂N-C₆H₄ | A2 | Chlorohydrate |

TABLE 3

| Comp N° | A ring | D ring | R³ | Synthesis Scheme | Salt Form |
|---|---|---|---|---|---|
| 96 | pyrimidine | phenyl | 4-O₂N-C₆H₄ | A | |
| 97 | 5-hydroxy-pyrimidine | phenyl | 4-O₂N-C₆H₄ | A3 | Bromohydrate |

TABLE 3-continued

| Comp N° | (R¹)ₘ―A―N (ring with positions 1,2) | D ring with (R²)ₙ | R³ | Synthesis Scheme | Salt Form |
|---|---|---|---|---|---|
| 98 | thiazoline (S-1, N-2) | phenyl (4,3) | 4-O₂N-C₆H₄- | F | |
| 99 | pyrimidine-type (N-1, N-2) | phenyl (4,3) | 4-O₂N-C₆H₄- | A | |
| 100 | pyrimidine-type (N-1, N-2) | phenyl (4,3) | 2-methyl-pyridin-5-yl | A | |
| 101 | pyridine-type (N-1, N-2) | 4-bromophenyl | 4-O₂N-C₆H₄- | A5 | |
| 102 | pyridine-type (N-1, N-2) | 3,5-dimethoxyphenyl | 4-O₂N-C₆H₄- | A | |
| 103 | pyridine-type (N-1, N-2) | thiophene (3-S, 4) | 4-O₂N-C₆H₄- | E | |
| 104 | pyridine-type (N-1, N-2) | 4-methylphenyl | 4-O₂N-C₆H₄- | E | |

TABLE 3-continued
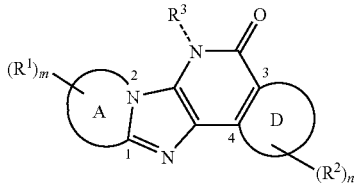
| Comp N° | (R¹)ₘ-A ring with N² | D ring with (R²)ₙ | R³ | Synthesis Scheme | Salt Form |
|---|---|---|---|---|---|
| 105 |  |  |  | E | |
| 106 |  |  |  | A | |
| 107 | 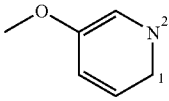 |  |  | E | |
| 108 | 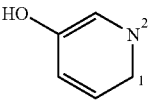 |  |  | E1 | |
| 109 | 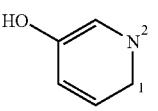 |  |  | E1 | |
| 110 | 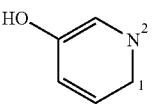 |  |  | E1 | Bromohydrate |
| 111 |  |  |  | E | |

TABLE 4

| Comp N° | R^1a | R^3 | Synthesis Scheme | Salt Form |
|---|---|---|---|---|
| 112 | methoxy | 4-nitrophenyl | A | |
| 113 | morpholin-4-yl | 4-nitrophenyl | D1 | |
| 114 | methylamino | 4-nitrophenyl | D1 | |
| 115 | 2-(pyrrolidin-1-yl)ethylamino | 4-nitrophenyl | D1 | |
| 116 | dimethylamino | 4-nitrophenyl | D1 | |
| 117 | 3-(morpholin-4-yl)propylamino | 4-nitrophenyl | D1 | |
| 118 | 3-hydroxypropylamino | 4-nitrophenyl | D1 | |
| 119 | 3-(imidazol-1-yl)propylamino | 4-nitrophenyl | D1 | |

TABLE 4-continued

| Comp N° | R$^{1a}$ | R$^3$ | Synthesis Scheme | Salt Form |
|---|---|---|---|---|
| 120 | (CH$_3$)$_2$N-CH$_2$CH$_2$CH$_2$-NH- | 4-O$_2$N-C$_6$H$_4$- | D1 | |
| 121 | HO-CH$_2$CH$_2$-NH- | 4-O$_2$N-C$_6$H$_4$- | D1 | |
| 122 | (CH$_3$)$_2$N-CH$_2$CH$_2$-NH- | 4-O$_2$N-C$_6$H$_4$- | D1 | |
| 123 | 3-hydroxy-pyrrolidin-1-yl | 4-O$_2$N-C$_6$H$_4$- | D1 | |
| 124 | (CH$_3$)$_2$N- | 2-Cl-pyridin-5-yl | D1 | |
| 125 | PhCH$_2$-NH- | 4-O$_2$N-C$_6$H$_4$- | D2 | |
| 126 | HO-CH$_2$CH$_2$-NH- | 2-Cl-pyridin-5-yl | D1 | |

TABLE 4-continued

| Comp N° | R¹ᵃ | R³ | Synthesis Scheme | Salt Form |
|---|---|---|---|---|
| 127 | methylamino | 2-chloropyridin-5-yl | D1 | |
| 128 | ethylaminoethylamino | 4-nitrophenyl | D1 | |
| 129 | H₂N– | 4-nitrophenyl | D2 | |
| 130 | HO-CH₂CH₂-NH-CH₂CH₂-NH– | 4-nitrophenyl | D1 | |
| 131 | H₂N– | 2-chloropyridin-5-yl | D2 | |

The following Table 5 lists a number of compounds of the invention, identified by the compound number as listed in the above tables 1-4, with corresponding NMR data:

NMR Data

| Comp N° | ¹HNMR (δ, DMSO–D6) |
|---|---|
| 1 | 6.65-6.69 (1H, m), 6.72-6.74 (1H, m), 7.21 (1H, dd, J ≈ 8 Hz, J ≈ 8 Hz), 7.65 (1H, t, J = 7.6 Hz), 7.70 (1H, d, J = 9.2 Hz), 7.96 (1H, t, J = 8.8 Hz), 8.00 (2H, d, J = 8.7 Hz), 8.35 (1H, d, J = 8.5 Hz), 8.37 (1H, d, J = 8.0 Hz), 8.54 (2H, d, J = 8.7 Hz) |
| 3 | 0.75 (3H, s), 6.41 (1H, s), 7.09 (1H, d, J = 9.4 Hz), 7.63-7.66 (2H, m), 7.95 (1H, t, J ≈ 8 Hz), 7.99 (2H, d, J = 8.9 Hz), 8.33-8.37 (2H, m), 8.54 (2H, d, J = 8.9 Hz) |
| 6 | 4.24 (2H, s), 5.14 (1H, s(br)), 6.60 (1H, s), 7.10 (1H, d, J = 9.4 Hz), 7.62-7.66 (2H, m), 7.94 (1H, t, J = 7.6 Hz), 8.01 (2H, d, J = 8.7 Hz), 8.32-8.36 (2H, m), 8.55 (2H, d, J = 8.7 Hz) |
| 7 | 6.64-6.65 (1H, m), 7.35 (1H, t, J ≈ 9 Hz), 7.68 (1H, t, J ≈ 8 Hz), 7.84 (1 H, dd, J = 9.9, 5.5 Hz), 7.96-8.01 (3H, m), 8.35-8.39 (2H, m), 8.55 (2H, d, J = 8.9 Hz) |

| Comp N° | ¹HNMR (δ, DMSO–D6) |
|---|---|
| 8 | 3.26 (3H, s), 6.10 (1H, d, J = 2.1 Hz), 7.04 (1H, dd, J = 9.8, 2.3 Hz), 7.62 – 7.68 (2H, m), 7.95 (1H, t, J = 7.3 Hz), 8.04 (2H, d, J = 8.8 Hz), 8.34 (2H, d, J ≈ 8 Hz), 8.56 (2H, d, J = 8.8 Hz) |
| 9 | 4.49 (2H, s), 5.44 (1H, s(br)), 6.60 (1H, dd, J = 7.4, 1.5 Hz), 6.68 (1H, d, J = 7.4 Hz), 7.55 (1H, s), 7.64 (1H, t, J = 7.6 Hz), 7.95 (1H, t, J ≈ 8 Hz), 7.98 (2H, d, J = 8.9 Hz), 8.34 (1H, d, J ≈ 8 Hz), 8.37 (1H, d, J ≈ 8 Hz), 8.53 (2H, d, J = 8.9 Hz) |
| 11 | 3.76 (3H, s), 7.34 (1H, s), 7.66 (1H, d, J = 9.5 Hz), 7.81 (1H, t, J = 7.6 Hz), 7.88 (1H, d, J = 9.6 Hz), 8.09 (1H, t, J = 7.6 Hz), 8.17 (2H, d, J = 8.6 Hz), 8.49 (1H, d, J = 7.7 Hz), 8.50 (1H, d, J = 7.6 Hz), 8.71 (2H, d, J = 8.6 Hz) |
| 18 | 6.76 (1H, t, J = 7.0 Hz), 6.93 (1H, d, J = 7.2 Hz), 7.23-7.25 (1H, m), 7.66 (1H, t, J = 7.6 Hz) 7.72 (1H, d, J = 9.2 Hz), 7.91 (1H, d, J = 8.5 Hz), 7.96 (1H, t, J = 7.6 Hz), 8.26 (1H, dd, J = 8.5, 2.7 Hz), 8.34 (1H, d, J = 8.0 Hz), 8.38 (1H, d, J = 7.8 Hz), 8.78 (1H, d, J = 2.6 Hz) |
| 19 | 2.68 (3H, s), 6.69-6.76 (2H, m), 7.20 (1H, ddd, J = 9.1, 6.4, 1.4 Hz), 7.61 (1H, d, J = 8.3 Hz), 7.65 (1H, t, J = 7.2 Hz), 7.70 (1H, d, J = 9.2 Hz), 7.95 (1H, td, J = 7.6, 0.9 Hz), 8.03 (1H, dd, J = 8.2, 2.5 Hz), 8.34 (1H, d, J = 8.0 Hz), 8.37 (1H, d, J = 7.9 Hz), 8.74 (1H, d, J = 2.4 Hz) |
| 20 | 6.64-6.66 (1H, m), 6.69-6.72 (1H, m), 7.21 (1H, ddd, J = 9.0, 6.5, 1.1 Hz), 7.66 (1H, td, J ≈ 9, 1.0 Hz), 7.71 (1H, d, J = 9.2 Hz), 7.79 (1H, dd, J = 8.0, 4.9 Hz), 7.96 (1H, td, J ≈ 8, 1.1 Hz), 8.19 (1H, ddd, J = 8.1, 2.3, 1.6 Hz), 8.35 (1H, d, J = 8.1 Hz), 8.38 (1H, d, J = 7.9 Hz), 8.89 (1H, dd, J = 4.8, 1.4 Hz), 8.91 (1H, d, J = 2.3 Hz) |
| 23 | 4.01 (3H, s), 6.74 (1H, t, J ≈ 7 Hz), 6.90 (1H, d, J = 7 Hz), 7.16 (1H, d, J = 8.7 Hz), 7.18-7.22 (1H, m), 7.64 (1H, t, J = 7.5 Hz), 7.70 (1H, d, J = 9.2 Hz), 7.94 (1H, t, J = 7.6 Hz), 8.05 (1H, dd, J = 8.7, 2.6 Hz), 8.33-8.38 (2 H, m), 8.49 (1H, d, J = 2.5 Hz) |
| 24 | 3.96 (3H, s), 6.60-6.61 (1H, m), 6.67-6.70 (1H, m), 7.18-7.22 (1H, m), 7.64-7.71 (2H, m), 7.85 (2H, d, J = 8.4 Hz), 7.95 (1H, t, J ≈ 7 Hz), 7.85 (2 H, d, J = 8.4 Hz), 8.34-8.39 (2H, m) |
| 25 | 6.69 (1H, d, J = 7.2 Hz), 6.85 (1H, t, J ≈ 7 Hz), 7.38 (1H, dd, J ≈ 8, ≈8 Hz), 7.71 (1H, t, J = 7.6 Hz), 7.80-7.84 (3H, m), 8.00 (1H, t, J = 7.6 Hz), 8.24 (2H, d, J = 8.5 Hz), 8.38 (1H, d, J = 8.0 Hz), 8.42 (1H, d, J = 7.7 Hz) |
| 28 | 2.77 (3H, s), 6.68-6.71 (1H, m), 6.79-6.81 (1H, m), 7.23 (1H, dd, J = 9.2, 6.6 Hz), 7.67 (1H, t, J = 7.6 Hz), 7.73 (1H, d, J = 9.1 Hz), 7.98 (1H, t, J = 7.4 Hz), 8.26-8.28 (1H, m), 8.33-8.37 (2H, m), 8.39 (1H, d, J = 7.9 Hz), 9.05 (1H, d, J = 2.3 Hz) |
| 29 | 6.64-6.66 (1H, m), 6.70-6.73 (1H, m), 7.22 (1H, dd, J ≈ 8, ≈8 Hz), 7.66 (1H, t, J = 7.8 Hz), 7.72 (1H, d, J = 9.3 Hz), 7.92 (1H, t, J ≈ 8 Hz), 7.97 (1 H, t, J ≈ 8 Hz), 8.07 (1H, d, J = 8.0 Hz), 8.19 (1H, d, J = 7.8 Hz), 8.30 (1 H, s), 8.35 (1H, d, J = 8.2 Hz), 8.38 (1H, d, J = 7.8 Hz) |
| 34 | 2.43 (3H, s), 6.68-6.73 (2H, m), 7.19 (1H, dd, J ≈ 8, ≈8 Hz), 7.44 (1 H, d, J = 8.0 Hz), 7.60-7.70 (4H, m), 7.94 (1H, t, J = 7.6 Hz), 8.33-8.37 (2H, m) |
| 35 | 6.63 (1H, d, J = 1.8 Hz), 7.34 (1H, dd, J = 9.8, 1.8 Hz), 7.75 (1H, t, J ≈ 8 Hz), 7.86 (1H, d, J = 9.8 Hz), 8.03-8.13 (3H, m), 8.34 (1H, d, J = 7.9 Hz) 8.38 (1H, d, 7.7 Hz), 8.73 (1H, d, J = 2.5 Hz), 10.28 (1H, s(br)) |
| 42 | 6.25 (1H, s), 7.16 (1H, d, J = 9.7 Hz), 7.58 (1 H, t, J ≈ 8 Hz), 7.64 (1H, d, J = 9.7 Hz), 7.75 (2H, d, J = 8.4 Hz), 7.87 (1H, t, J ≈ 8 Hz), 8.08 (2H, d, J = 8.3 Hz), 8.22 (1H, d, J = 8.0 Hz), 8.35 (1H, d, J = 7.9 Hz), 10.17 (1H, s(br)) |
| 43 | 2.89 (3H, s), 6.95 (1H, s), 7.48 (1H, d, J = 9.6 Hz), 7.86 (1H, t, J = 7.4 Hz), 7.92 (1H, d, J = 9.6 Hz), 7.98 (1H, d, J = 8.3 Hz), 8.13 (1H, t, J = 7.0 Hz), 8.40 (1H, d, J = 8.3 Hz), 8.46 (1H, d, J = 7.7 Hz), 8.63 (1H, d, J = 7.7 Hz), 9.03 (1H, s), 10.78 (1H, s(br)) |
| 47 | 4.30 (2H, s), 6.36 (1H, s), 7.38 (1H, d, J = 9.6 Hz), 7.69 (4H, s), 7.73 (1H, t, J ≈ 8 Hz), 7.81 (1H, d, J = 9.8 Hz), 8.02 (1H, t, J ≈ 8 Hz), 8.38 (1H, d, J = 7.9 Hz), 8.49 (1H, d, J = 7.9 Hz), 10.35 (1H, s(br)) |
| 50 | 2.38 (3H, s), 6.85 (1H, s), 7.79-7.83 (2H, m), 8.00 (1H, d, J = 8.5 Hz), 8.11 (1H, t, J ≈ 8 Hz), 8.26 (1H, dd, J = 8.5, 2.5 Hz), 8.44 (1H, d, J = 7.9 Hz), 8.59 (1H, d, J = 7.9 Hz), 8.80 (1H, d, J = 2.5 Hz), 10.65 (1H, s) |
| 53 | 5.07 (2H, s(br)) 6.28 (1H, m), 6.91 (1H, dd, J = 9.7, 2.0 Hz), 7.55 (1H, d, J = 9.6 Hz), 7.64 (1H, td, J = 7.6, 1.1 Hz), 7.91 (1H, d, J = 8.4 Hz), 7.96 (1H, td, J = 7.6, 1.1 Hz), 8.22 (1H, dd, J = 8.4, 2.7 Hz), 8.34-8.36 (2H, m), 8.77 (1 H, d, J = 2.7 Hz) |
| 54 | 3.38 (3H, s), 6.18 (1H, d, J ≈ 2 Hz), 7.07 (1H, dd, J = 9.9, ≈2 Hz), 7.62-7.68 (2H, m), 7.93-7.97 (2H, m), 8.30-8.35 (3H, m), 8.83 (2H, d, J = 2.5 Hz) |
| 56 | 1.89 (3H, s), 7.05 (1H, d, J = 9.6 Hz), 7.62-7.68 (2H, m), 7.94-7.96 (3 H, m), 8.33-8.35 (2H, m), 8.53-8.55 (2H, m), 9.90 (1H, s) |
| 57 | 7.09 (1H, d, J = 9.7 Hz), 7.64 (1H, t, J = 7.6 Hz), 7.70 (1H, d, J = 9.7 Hz), 7.88 (1H, d, J = 8.4 Hz), 7.95 (1H, t, J = 7.6 Hz), 8.14 (1H, s), 8.18 (1H, s), 8.23 (1H, dd, J = 8.4, ≈2 Hz), 8.32-8.35 (2H, m), 8.73 (1H, d, J ≈ 2 Hz), 10.31 (1H, s) |
| 58 | 6.81-6.81 (1H, m), 7.37 (1H, t, J ≈ 8 Hz ), 7.68 (1H, t, J = 7.4 Hz), 7.84 (1 H, dd, J = 10.0, 5.4 Hz), 7.92-7.94 (1H, m), 7.96-7.99 (1H, m), 8.26(1H, dd, J ≈ 9, 2.0 Hz), 8.34-8.38 (2H, m), 8.78 (1H, d, J = 2.4 Hz) |
| 60 | 1.03 (3H, t, J = 7.1 Hz), 3.04 (2H, p, J ≈ 7 Hz), 6.07-6.10 (1H, m), 6.97 (1 H, dd, J = 9.7, 1.3 Hz), 7.58-7.64 (2H, m), 7.78 (1H, s), 7.86 (1H, d, J = 8.4 Hz), 7.93 (1H, t, J = 7.6 Hz), 8.19 (1H, dd, J = 8.4, 2.5 Hz), 8.31-8.33 (2 H, m), 8.43 (1H, s), 8.70 (1H, d, J = 2.5 Hz) |

-continued

| Comp N° | ¹HNMR (δ, DMSO-D6) |
|---|---|
| 61 | 7.35 (1H, dd, J = 9.8, 1.8 Hz), 7.65 (1H, t, J = 7.6 Hz), 7.77 (1H, d, 9.8 Hz), 7.92 (1H, d, J = 8.5 Hz), 7.95 (1H, t, J = 7.5 Hz), 8.00 (1H, s), 8.25 (1H, dd, J = 8.3, 2.6 Hz), 8.33-8.36 (2 H,m), 8.76 (1H, d, J = 2.5 Hz), 11.39 (1H, s) |
| 63 | 2.44 (3H, s), 6.43 (1H, s), 7.27-7.29 (1H, m), 7.40 (1H, d, J = 8.0 Hz), 7.64-7.57 (2H, m), 7.70 (1H, t, J = 7.6 Hz), 7.75 (1H, d, J = 9.8 Hz), 7.99 (1H, t, J = 7.6 Hz), 8.36 (1H, d, J = 7.9 Hz), 8.46 (1H, d, J = 7.7 Hz), 10.25 (1 H, s(br)) |
| 72 | 7.27 (1H, s(br)), 7.41 (1H, s(br)), 7.63-7.75 (3H, m), 7.95-7.99 (2H, m), 8.04 (2H, d, J = 8.6 Hz), 8.35-8.39 (2H, m), 8.58 (2H, d, J = 8.5 Hz) |
| 73 | 2.00 (3H, s), 3.60 (2H, dd, J ≈ 4.7, ≈4.7 Hz), 4.12 (2H, dd, J ≈ 4.6, ≈4.6 Hz), 6.12 (1H, d, J = 1.8 Hz), 7.08 (1H, dd, J = 9.9, 2.3 Hz), 7.63-7.69 (2H, m), 7.95 (1H, td, J = 7.6, 1.3 Hz), 8.03 (2H, d, J = 9.0 Hz), 8.35 (2H, d, J ≈ 8 Hz), 8.54 (2H, d, J = 9.0 Hz) |
| 77 | 4.50 (2H, s(br)), 6.96 (1H, s), 7.19 (1H, dd, J = 9.8, 2.0 Hz), 7.67 (1H, t, J ≈ 8 Hz), 7.76 (1H, d, J = 9.8 Hz), 7.85 (1H, d, J = 8.5), 7.97 (1H, t, J ≈ 8), 8.23 (1H, dd, J = 8.5, 2.6 Hz), 8.34-8.40 (2H, m), 8.76 (1H, d, J = 2.6 Hz) |
| 78 | 1.64-1.66 (4H, m), 2.32-2.35 (4H, m), 3.41-3.45 (4H, m), 6.09 (1H, d, J = 2.1 Hz), 7.04 (1H, dd, J = 9.8, 2.3 Hz), 7.62-7.67 (2H, m), 7.95 (1H, t, J = 7.6 Hz), 8.04 (2H, d, J = 8.9 Hz), 8.35 (1H, d, J = 7.8 Hz), 8.34 (1H, d, J = 7.8 Hz), 8.57 (2H, d, J = 8.9 Hz) |
| 81 | 2.07 (6H, s), 6.05-6.10 (1H, m), 7.02-7.06 (1H, m), 7.64-7.68 (2H, m), 7.95 (1H, t, J ≈ 8 Hz), 8.04 (2H, d, J = 8.9 Hz), 8.34 (1H, d, J = 8.3 Hz), 8.35 (1H, d, J = 7.7 Hz), 8.57 (2H, d, J = 8.9 Hz) |
| 86 | 0.87 (3H, t, J = 7.2 Hz), 1.13-1.28 (4H, m), 1.37-1.44 (2H, m), 2.15 (2H, t, J = 7.1 Hz), 7.04 (1H, d, J = 9.7), 7.62-7.67 (2H, m), 7.89 (1H, s), 7.93-7.96 (3H, m), 8.34 (1H, d, J = 7.6 Hz), 8.35 (1H, d, J = 7.7 Hz), 8.53 (2H, d, J = 8.7 Hz), 9.87 (1H, s) |
| 88 | 5.19 (1H, s(br)) 6.41 (1H, s(£r)), 7.42 (1H, dd, J = 9.7, 1.6 Hz), 7.81 (1H, t, J ≈ 8 Hz), 7.90 (1H, d, J = 9.6 Hz), 8.02 (2H, d, J = 8.9 Hz), 8.10 (1H, t, J ≈ 8 Hz), 8.44 (1H, d, J = 8.0 Hz), 8.57 (1H, d, J = 7.9 Hz), 8.62 (2H, d, J = 8.9 Hz) |
| 90 | 7.37 (1H, d, J = 10.0 Hz), 7.72 (1H, t, J = 7.7 Hz), 7.82 (1H, d, J = 9.9 Hz), 7.83 (1H, s), 8.01 (1H, t, J = 7.5 Hz), 8.06 (2H, d, J = 8.7 Hz), 8.42 (2H, d, J ≈ 8 Hz), 8.63 (2H, d, J = 8.7 Hz), 11.38 (1H, s(br)) |
| 92 | 3.97 (3H, s), 6.86 (1H, t, J = 7.1 Hz), 7.19 (1H, d, J = 7.1 Hz), 7.69 (1H, t, J ≈ 8 Hz), 7.80 (1H, d, J = 7.1 Hz) 7.91 (1H, d, J = 8.4 Hz), 7.99 (1H, t, J ≈ 8 Hz), 8.25 (1H, dd, J = 8.4 Hz, J = 2.4 Hz), 8.35 (1H, d, J = 7.9 Hz), 8.40 (1H, d, J = 7.8 Hz), 8.77 (1H, d, J = 2.3 Hz) |
| 93 | 6.70 (1H, t, J = 7.2 Hz), 6.99 (1H, d, J = 7.0 Hz), 7.62 (1H, d, J = 7.0 Hz), 7.69 (1H, t, J ≈ 8 Hz), 7.91 (1H, d, J = 8.3 Hz), 7.99 (1H, t, J ≈ 8 Hz), 8.24 (1H, dd, J = 8.3, 2.6 Hz), 8.36 (1H, d, J = 7.6 Hz), 8.43 (1H, d, J = 8.1 Hz), 8.76 (1H, d, J = 2.3 Hz) |
| 106 | 6.45-6.52 (2H, m), 7.00-7.04 (1H, m), 7.50 (1H, d, J = 9.2 Hz), 7.72 (1 H, dd, J = 8.0, 4.5 Hz), 7.79 (2H, d, J = 8.9 Hz), 8.34 (2H, d, J = 8.9 Hz), 8.54 (1H, dd, J = 8.1, 1.6 Hz), 8.70 (1H, dd, J = 4.3, 1.6 Hz) |
| 108 | 1.36 (3H, t, J = 7.3 Hz), 3.65 (2H, q, J = 7.4 Hz), 6.22 (1H, s), 6.96 (1H, d, J = 9.6 Hz), 7.55 (1H, t, J ≈ 8 Hz), 7.65 (1H, d, J = 9.8 Hz), 7.76 (1H, d, 7.3 Hz), 7.95 (2H, d, J = 8.4 Hz), 8.26 (1H, d, J = 7.9 Hz), 8.56 (2H, d, J = 8.4 Hz), 9.56 (1H, s(br)) |
| 113 | 2.90 (4H, s(br)), 3.45 (4H, s(br)), 7.13 (1H, d, J = 10.1 Hz), 7.62 (1H, t, J ≈ 8 Hz), 7.88-7.98 (4H, m), 8.30 (1H, d, J = 8.0 Hz), 8.34 (1H, d, J = 8.2 Hz), 8.42 (2H, d, J = 8.7 Hz) |
| 121 | 3.03 (2H, td, J ≈ 5, ≈5 Hz), 4.52 (1H, t, J ≈ 5 Hz), 6.64 (1H, d, J = 9.8 Hz), 7.00 (1H, t, J ≈ 6 Hz), 7.58 (1H, t, J = 8.0 Hz), 7.75 (1H, d, J = 9.8 Hz), 7.86 (2H, d, J = 8.8 Hz), 7.91 (1H, t, J = 7.2 Hz), 8.26 (1H, d, J = 7.8 Hz), 8.31 (1H, d, J = 7.9 Hz), 8.39 (2H, d, J = 8.8 Hz) |

Antiviral Analyses

The compounds of the present invention were tested for anti-viral activity in a cellular assay, which was performed according to the following procedure.

The human T-cell line MT4 is engineered with Green Fluorescent Protein (GFP) and an HIV-specific promoter, HIV-1 long terminal repeat (LTR). This cell line is designated MT4 LTR-EGFP, and can be used for the in vitro evaluation of anti-HIV activity of investigational compounds. In HIV-1 infected cells, the Tat protein is produced which upregulates the LTR promotor and finally leads to stimulation of the GFP reporter production, allowing to measure ongoing HIV-infection fluorometrically.

Analogously, MT4 cells are engineered with GFP and the constitutional cytomegalovirus (CMV) promotor. This cell line is designated MT4 CMV-EGFP, and can be used for the in vitro evaluation of cytotoxicity of investigational compounds. In this cell line, GFP levels are comparably to those of infected MT4 LTR-EGFP cells. Cytotoxic investigational compounds reduce GFP levels of mock-infected MT4 CMV-EGFP cells.

Effective concentration values such as 50% effective concentration (EC50) can be determined and are usually expressed in μM. An EC50 value is defined as the concentration of test compound that reduces the fluorescence of HIV-infected cells by 50%. The 50% cytotoxic concentration ($CC_{50}$ in μM) is defined as the concentration of test compound that reduces fluorescence of the mock-infected cells by 50%. The ratio of $CC_{50}$ to $EC_{50}$ is defined as the selectivity index (SI) and is an indication of the selectivity of the anti-HIV activity of the inhibitor. The ultimate monitoring of HIV-1 infection and cytotoxicity is done using a scanning microscope. Image analysis allows very sensitive detection of viral infection. Measurements are done before cell necrosis, which usually takes place about five days after infection, in particular measurements are performed three days after infection.

The following Table 6 lists $pEC_{50}$ values against wild-type HIV-IIIB strain as well as $pEC_{50}$ values for a selected number of compounds of the invention. A pEC50 value corresponds to $-\log_{10}(EC50)$. Listed are compounds having a pEC50 value of at least 5.00.

TABLE 6

Antiviral activity

| Comp N° | $pEC_{50}$ | $pCC_{50}$ |
| --- | --- | --- |
| 1 | 6.45 | <4.49 |
| 9 | 6.14 | <4.49 |
| 10 | 6.81 | <4.49 |
| 12 | 5.38 | <4.49 |
| 18 | 5.09 | <4.49 |
| 19 | 5.05 | <4.49 |
| 21 | 5.35 | <4.49 |
| 22 | 5.54 | <4.49 |
| 27 | 5.24 | 4.58 |
| 35 | 5.57 | <4.49 |
| 37 | 5.15 | <4.49 |
| 42 | 5.18 | <4.49 |
| 43 | 5.43 | <4.49 |
| 44 | 5.84 | <4.49 |
| 46 | 5.35 | <4.49 |
| 47 | 5.44 | <4.49 |
| 48 | 5.40 | 4.50 |
| 49 | 6.41 | <4.49 |
| 50 | 5.79 | 4.52 |
| 53 | 5.78 | 5.34 |
| 61 | 5.68 | <4.49 |
| 63 | 5.24 | <4.49 |
| 64 | 5.97 | 4.84 |
| 65 | 5.44 | 5.21 |
| 67 | 6.47 | 5.58 |
| 68 | 5.91 | 4.78 |
| 70 | 6.22 | <4.49 |
| 74 | 6.06 | <4.49 |
| 76 | 7.13 | <4.49 |
| 77 | 5.95 | 4.59 |
| 78 | 5.52 | <4.49 |
| 81 | 5.50 | 4.87 |
| 82 | 5.95 | 5.05 |
| 84 | 5.21 | 4.78 |
| 88 | 7.15 | <4.49 |
| 90 | 6.40 | <4.49 |
| 96 | 5.46 | <4.00 |
| 98 | 6.01 | <4.49 |
| 99 | 5.35 | <4.00 |
| 101 | 5.66 | <4.00 |
| 102 | 5.78 | <4.49 |
| 103 | 6.00 | <4.49 |
| 104 | 6.39 | <4.49 |
| 105 | 5.67 | <4.49 |
| 106 | 5.50 | <4.49 |
| 108 | 5.64 | <4.49 |
| 109 | 5.91 | 4.50 |
| 110 | 7.27 | 5.27 |
| 111 | 5.46 | <4.49 |
| 114 | 6.61 | <4.49 |
| 115 | 6.04 | 6.08 |
| 118 | 6.19 | <4.49 |
| 120 | 6.20 | 5.88 |
| 121 | 6.56 | 4.83 |
| 122 | 7.05 | 7.16 |
| 125 | 5.28 | <4.70 |
| 126 | 5.67 | <4.49 |
| 128 | 7.51 | 6.07 |
| 129 | 6.78 | <4.49 |
| 130 | 6.66 | 5.45 |
| 131 | 6.10 | 4.59 |

Formulations
Capsules

Compound 1 is dissolved in a mixture of ethanol and methylene chloride and hydroxypropylmethylcellulose (HPMC) 5 mPa·s is dissolved in ethanol. Both solutions are mixed such that the w/w ratio compound/polymer is 1/3 and the mixture is spray dried in standard spray-drying equipment. The spray-dried powder, a solid dispersion, is subsequently filled in capsules for administration. The drug load in one capsule is selected such that it ranges between 50 and 100 mg, depending on the capsule size used. Following the same procedures, capsule formulations of the other compounds of formula (I) can be prepared.

Film-Coated Tablets
Preparation of Tablet Core

A mixture of 1000 g of compound 1, 2280 g lactose and 1000 g starch is mixed well and thereafter humidified with a solution of 25 g sodium dodecyl sulfate and 50 g polyvinylpyrrolidone in about 1000 ml of water. The wet powder mixture is sieved, dried and sieved again. Then there is added 1000 g microcrystalline cellulose and 75 g hydrogenated vegetable oil. The whole is mixed well and compressed into tablets, giving 10,000 tablets, each comprising 100 mg of the active ingredient.

Coating

To a solution of 10 g methylcellulose in 75 ml of denaturated ethanol there is added a solution of 5 g of ethylcellulose in 150 ml of dichloromethane. Then there is added 75 ml of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinylpyrrolidone and 30 ml of concentrated color suspension and the whole is homogenated. The tablet cores are coated with the thus obtained mixture in a coating apparatus.

Following the same procedures, tablet formulations of the other compounds of formula (I) can be prepared.

The invention claimed is:

1. A compound of formula (I):

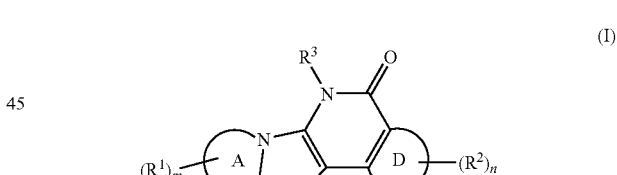

a stereoisomeric forms or stereoisomeric mixture thereof, a pharmaceutically acceptable salt thereof, an N-oxide thereof, wherein A forms, together with the nitrogen and carbon atoms of the ring system to which it is attached, an aromatic heterocycle selected from pyridine, pyrimidine, pyrazine, pyridazine, triazine, imidazole, pyrazole, triazole, tetrazole, oxazole, isoxazole, oxadiazole, thiazole, isothiazole, and thiadiazole;

each $R^1$ is, independently, a radical selected from halo, cyano, nitro, $C_{1-6}$alkyl, polyhalo$C_{1-6}$alkyl, —$C_{1-6}$alkyl-$OR^4$, —C(=O)—$R^5$, —C(=O)—$OR^4$, —C(=O)—$NR^6R^7$, —$OR^4$, —O—C(=O)—$C_{1-6}$alkyl, —O—$C_{1-6}$alkyl-$OR^4$, —O—$C_{1-6}$alkyl-$NR^6R^7$, —O—$C_{1-6}$alkyl-O—C(=O)—$C_{1-6}$alkyl, —O—$C_{1-6}$alkyl-C(=O)—$OR^4$, —O—$C_{1-6}$alkyl-C(=O)—$NR^6R^7$, —$NR^6R^7$, —$NR^8$—C(=O)—$R^5$, —$NR^8$—C(=O)—$OR^4$, —NR$^8$—C(=O)—NR$^6$R$^7$, —NR$^8$—C(=O)—C$_{1-6}$alkyl-C(=O)—OR$^4$, —NR$^8$—C$_{1-6}$alkyl-OR$^4$, —NR$^8$—C$_{1-6}$alkyl-NR$^6$R$^7$, —NR$^8$—C$_{1-6}$alkyl-imidazolyl, —NR$^8$—SO$_2$R$^9$, —N=CH—NR$^6$R$^7$, —NH—C(=NH)—NH$_2$, —SO$_2$NR$^6$R$^7$, and —O—PO(OR$^8$)$_2$;

D forms, together with the two carbon atoms of the ring system to which it is attached, an aromatic ring selected from phenyl, pyridine, pyrimidine, pyrazine, pyridazine, pyrrole, imidazole, pyrazole, furane, oxazole, isoxazole, thiophene, thiazole, and isothiazole;

each R$^2$ is, independently, a radical selected from C$_{1-6}$alkyl, polyhaloC$_{1-6}$alkyl, halo, cyano, —COOR$^4$, —OR$^4$, and —NR$^6$R$^7$;

R$^3$ is phenyl, pyridyl, pyrimidinyl, imidazopyridyl, pyrazolopyridyl, triazolopyridyl, quinoline, imidazopyrimidinyl, pyrazolopyrimidinyl, triazolopyrimidinyl, pyridopyrimidinyl; wherein said phenyl, pyridyl, or pyrimidinyl, may optionally be substituted with 1, 2, or 3 substituents selected from C$_{1-6}$alkyl; C$_{2-6}$alkenyl; C$_{2-6}$alkynyl; polyhaloC$_{1-6}$alkyl; C$_{1-6}$alkyl substituted with one or two cyano or hydroxy; halo; cyano; nitro; —C(=O)—R$^5$; —C(=O)—OR$^4$; —C(=O)—NR$^6$R$^7$; —OR; —NR$^6$R$^7$; and wherein said imidazopyridyl, pyrazolopyridyl, triazolopyridyl, quinoline, imidazopyrimidinyl, pyrazolopyrimidinyl, triazolopyrimidinyl, pyridopyrimidinyl, may optionally be substituted with 1 or 2 substituents selected from C$_{1-6}$alkyl, halo, amino, and —OR$^4$;

m represents 0, 1, 2 or 3;

n represents 0, 1, 2 or 3;

each R$^4$ is hydrogen, C$_{1-6}$alkyl or arylC$_{1-6}$alkyl;

each R$^5$ is hydrogen, C$_{1-6}$alkyl or polyhaloC$_{1-6}$alkyl;

each R$^6$ is hydrogen or C$_{1-6}$alkyl;

each R$^7$ is hydrogen, C$_{1-6}$alkyl optionally substituted with hydroxy, aryl, mono- or diC$_{1-16}$alkylamino, morpholinyl, thiomorpholinyl, piperidinyl, piperazinyl, 4-C$_{1-6}$alkyl-piperazinyl, 4-C$_{1-6}$alkylcarbonyl-piperazinyl or with pyrrolidinyl; or R$^6$ and R$^7$ taken together with the nitrogen on which they are substituted form pyrrolidinyl, hydroxypyrrolidinyl, piperidinyl, morpholinyl, thiomorpholinyl, piperazinyl, 4-C$_{1-6}$alkyl-piperazinyl, 4-C$_{1-6}$alkylcarbonyl-piperazinyl;

each R$^8$ is hydrogen or C$_{1-6}$alkyl;

each R$^9$ is C$_{1-6}$alkyl;

each aryl is phenyl optionally substituted with 1, 2, or 3 substituents independently selected from C$_{1-6}$alkyl, halo, and hydroxy.

2. A compound according to claim 1 wherein A forms, together with the nitrogen and carbon atoms of the ring system to which it is attached, an aromatic heterocycle selected from pyridine, pyrimidine, pyridazine, and thiazole.

3. A compound according to claim 1, wherein each R$^1$ is, independently, a radical selected from C$_{1-6}$alkyl, —C$_{1-6}$alkyl-OR$^4$, —OR$^4$, —O—C$_{1-6}$alkyl-OR$^4$, —O—C$_{1-6}$alkyl-NR$^6$R$^7$, —NR$^6$R$^7$, —NR$^8$—C(=O)—R$^5$, —NR$^8$—C$_{1-6}$alkyl-OR$^4$, —NR$^8$—C$_{1-6}$alkyl-NR$^6$R$^7$, and —O—PO(OR$^8$)$_2$.

4. A compound according to claim 1, wherein m is 0, 1 or 2 and/or n is 0 or 1.

5. A compound according to claim 1, wherein D forms, together with the two carbon atoms of the ring system to which it is attached, an aromatic ring selected from phenyl, pyridine, and thiophene.

6. A compound according to claim 1, wherein each R$^2$ is, independently, a radical selected from C$_{1-6}$alkyl, halo, and —OR$^4$.

7. A compound according to claim 1, wherein R$^3$ is phenyl, pyridyl, imidazopyridyl, imidazopyrimidinyl; wherein said phenyl or pyridyl may optionally be substituted with 1, 2 substituents selected from C$_{1-6}$alkyl; polyhaloC$_{1-6}$alkyl; C$_{1-6}$alkyl substituted with one or two cyano; halo; cyano; nitro; —C(=O)—R$^5$; —C(=O)—OR$^4$; —OR$^4$.

8. A compound according to claim 1, wherein each R$^6$ or R$^7$ independently is hydrogen or C$_{1-4}$alkyl.

9. A compound according to claim 1, wherein R$^5$ is hydrogen or C$_{1-4}$alkyl.

10. A compound according to claim 1, wherein R$^4$ is hydrogen or C$_{1-4}$alkyl.

11. A pharmaceutical composition comprising a carrier and as active ingredient a compound as claimed in claim 1.

* * * * *